(12) United States Patent
Spiller et al.

(10) Patent No.: US 11,083,818 B2
(45) Date of Patent: *Aug. 10, 2021

(54) METHODS FOR INDUCING MACROPHAGE CONVERSION IN A WOUND

(71) Applicant: Drexel University, Philadelphia, PA (US)

(72) Inventors: Kara L. Spiller, Philadelphia, PA (US); Sina Nassiri, Philadelphia, PA (US)

(73) Assignee: Drexel University, Philadelphia, PA (US)

(*) Notice: Subject to any disclaimer, the term of this patent is extended or adjusted under 35 U.S.C. 154(b) by 76 days.

This patent is subject to a terminal disclaimer.

(21) Appl. No.: 16/157,760

(22) Filed: Oct. 11, 2018

(65) Prior Publication Data

US 2019/0038800 A1    Feb. 7, 2019

Related U.S. Application Data

(62) Division of application No. 15/036,822, filed as application No. PCT/US2014/066517 on Nov. 20, 2014, now Pat. No. 10,098,982.

(60) Provisional application No. 61/906,630, filed on Nov. 20, 2013.

(51) Int. Cl.
| | | |
|---|---|---|
| A61K 38/20 | (2006.01) | |
| A61L 26/00 | (2006.01) | |
| A61L 27/20 | (2006.01) | |
| A61L 27/56 | (2006.01) | |
| C08L 5/04 | (2006.01) | |
| C08L 5/08 | (2006.01) | |
| C08L 89/00 | (2006.01) | |
| C08L 89/04 | (2006.01) | |

(52) U.S. Cl.
CPC ...... *A61L 26/0066* (2013.01); *A61K 38/2026* (2013.01); *A61K 38/2066* (2013.01); *A61L 26/008* (2013.01); *A61L 26/0023* (2013.01); *A61L 26/0038* (2013.01); *A61L 26/0047* (2013.01); *A61L 27/20* (2013.01); *A61L 27/56* (2013.01); *C08L 5/04* (2013.01); *C08L 5/08* (2013.01); *C08L 89/00* (2013.01); *C08L 89/04* (2013.01); *A61L 2300/252* (2013.01); *A61L 2300/258* (2013.01); *A61L 2300/426* (2013.01); *A61L 2300/608* (2013.01); *A61L 2300/622* (2013.01)

(58) Field of Classification Search
CPC .......... A61K 38/2026; A61K 38/2066
See application file for complete search history.

(56) References Cited

U.S. PATENT DOCUMENTS

| | | | |
|---|---|---|---|
| 7,285,266 B2 | 10/2007 | Vournakis et al. | |
| 7,363,075 B2 | 4/2008 | Stern et al. | |
| 7,713,544 B2 | 5/2010 | Chaikof et al. | |
| 7,816,316 B2 | 10/2010 | Hahn et al. | |
| 7,928,280 B2 | 4/2011 | Hariri et al. | |
| 8,029,774 B2 | 10/2011 | Beckman et al. | |
| 8,067,237 B2 | 11/2011 | Mooney et al. | |
| 8,080,418 B2 | 12/2011 | Noll et al. | |
| 8,246,998 B2 | 8/2012 | Ogara | |
| 8,247,384 B2 | 8/2012 | Green et al. | |
| 8,430,831 B2 | 4/2013 | Hyde et al. | |
| 8,440,185 B2 | 5/2013 | Chen et al. | |
| 8,518,879 B2 | 8/2013 | Al-Qahtani | |
| 8,557,271 B2 | 10/2013 | Kimble et al. | |
| 10,098,982 B2* | 10/2018 | Spiller | A61K 38/2026 |
| 2011/0268807 A1 | 11/2011 | Su et al. | |
| 2013/0252281 A1 | 9/2013 | De Fougerolles et al. | |
| 2013/0274578 A1 | 10/2013 | Klueh et al. | |

FOREIGN PATENT DOCUMENTS

| | | |
|---|---|---|
| WO | 2008121422 A2 | 10/2008 |
| WO | 2013102193 A1 | 7/2013 |
| WO | 2015031376 A1 | 3/2015 |

OTHER PUBLICATIONS

PCT International Search Report and Written Opinion for PCT International Application No. PCT/US2014/066517 dated Feb. 19, 2015.
Acosta, et al., "The pro-inflammatory environment in recalcitrant diabetic foot wounds", Int Wound J. 5(4), Oct. 2008, 530-539.
Ashley, G. W., et al., "Hydrogel drug delivery system with predictable and tunable drug release and degradation rates", Proc Natl Acad Sci USA. 110(6), Feb. 5, 2013, 2318-2323.
Balmert, et al., Biomimetic delivery with micro- and nanoparticles, Adv Mater. 24(28), Jul. 24, 2012, 3757-3778.
Beukelman, et al., "Anti-inflammatory properties of a liposomal hydrogel with povidone-iodine (Repithel) for wound healing in vitro", Burns. 34(6), Sep. 2008, 845-855.
Chen, et al., "In vitro cellular responses to scaffolds containing two microencapulated growth factors", Biomaterials. 30(28), Oct. 2009, 5215-5224.
Chen, et al., "Toward delivery of multiple growth factors in tissue engineering", Biomaterials. 31(24), Aug. 2010, 6279-6308.
Hanson, et al., "The effect of mesenchymal stromal cell-hyaluronic acid hydrogel constructs on immunophenotype of macrophages", Tissue Eng Part A. 17(19-20), Oct. 2011, 2463-2471.
Hirsch, et al., "Easily reversible desthiobiotin binding to streptavidin, avidin, and other biotin-binding proteins: uses for protein labeling, detection, and isolation", Anal Biochem. 308(2), Sep. 15, 2002, 343-357.
Hume, P. S., et al., "Strategies to reduce dendritic cell activation through functional biomaterial design", Biomaterials 33(14), May 2012, 3615-25.

(Continued)

*Primary Examiner* — Prema M Mertz
(74) *Attorney, Agent, or Firm* — Saul Ewing Arnstein & Lehr LLP; Kathryn Doyle; Brian R. Landry

(57) ABSTRACT

One aspect of the invention provides a method of sequentially inducing macrophage conversion in a wound. The method includes: (a) administering IL-4 to induce conversion of a first population of wound macrophages in the wound to M2A macrophages; and then (b) administering IL-10, dexamethasone, or a dexamethasone analog to induce conversion of a second population of wound macrophages in the wound to M2C macrophages.

14 Claims, 21 Drawing Sheets

(56) References Cited

OTHER PUBLICATIONS

Kay, et al., "An M13 phage library displaying random 38-amino-acid peptides as a source of novel sequences with affinity to selected targets", Gene. 128(1), Jun. 15, 1993, 59-65.

Kuhn, et al., "Binding of a diverse set of ligands to avidin and streptavidin: an accurate quantitative prediction of their relative affinities by a combination of molecular mechanics and continuum solvent models", J Med Chem. 43(20), Oct. 5, 2000, 3786-3791.

Liu, et al., "Controlled release of brefeldin A from electrospun PEG-PLLA nanofibers and their in vitro antitumor activity against HepG2 cells", Mater Sci Eng C Mater Biol Appl. 33(5), Jul. 1, 2013, 2513-2518.

Loftsson, et al., "Cyclodextrin microparticles for drug delivery to the posterior segment of the eye: aqueous dexamethasone eye drops", J Pharm Pharmacol. 59(5), May 2007, 629-635.

Loftsson, et al., "Cyclodextrins and their pharmaceutical applications", Int J Pharm. 329(1-2), Feb. 1, 2007, 1-11.

Loftsson, et al., "Cyclodextrins in drug delivery", Expert Opin Drug Deliv. 2(2), Mar. 2005, 335-351.

Loftsson, et al., "Effects of cyclodextrins on drug delivery through biological membranes", J Pharm Sci. 96(10), Oct. 2007, 2532-2546.

Loftsson, et al., "Evaluation of cyclodextrin solubilization of drugs", Int J Pharm. 302(1-2), Sep. 30, 2005, 18-28.

Meyer, et al. "Highly selective cyclic peptide ligands for NeutrAvidin and avidin identified by phage display", Chem Biol Drug Des. 68(1), Jul. 2006, 3-10.

Patterson, et al., "Enhanced proteolytic degradation of molecularly engineered PEG hydrogels in response to MMP-1 and MMP-2", Biomaterials 31(30), Oct. 2010, 7836-7845.

Sakiyama-Elbert, et al., "Development of fibrin derivatives for controlled release of heparin-binding growth factors", J Control Release. 65(3), Apr. 3, 2000, 389-402.

Sohier, et al., "Dual release of proteins from porous polymeric scaffolds", J Control Release. 111(1-2), Mar. 10, 2006, 95-106.

Song, et al., "Controllable delivery of hydrophilic and hydrophobic drugs from electrospun poly(lactic-co-glycolic acid)/mesoporous silica nanoparticles composite mats", J Biomed Mater Res B Appl Biomater. 100(8), Nov. 2012, 2178-2186.

Song, et al., "Dual drug release from electrospun poly(lactic-co-glycolic acid)/mesoporous silica nanoparticles composite mats with distinct release profiles", Acta Biomater. 8(5), May 2012, 1901-1907.

Soranno, D. E., et al., "Immunotherapy with injectable hydrogels to treat obstructive nephropath", J Biomed Mater Res A 102(7), Jul. 31, 2014, 2173-2180.

Spiller, et al., "The Role of Macrophage Phenotype in Vascularization of Tissue Engineering Scaffolds", Biomaterials. 35(15), May 2014, 4477-4488.

Stadelmann, et al., "Impediments to wound healing", Am J Surg. Aug. 1998;176(2A Suppl), Aug. 1998, 39S-47S.

Steenblock, et al., "An artificial antigen-presenting cell with paracrine delivery of IL-2 impacts the magnitude and direction of the T cell response", J Biol Chem. 286(40), Oct. 7, 2011, 34883-34892.

Wang, et al., "Modulation of the physicochemical state of interior agents to prepare controlled release liposomes", Colloids Surf B Biointerfaces. 69(2), Mar. 1, 2009, 232-238.

Willerth, et al., "Rationally designed peptides for controlled release of nerve growth factor from fibrin matrices", J Biomed Mater Res A. 80(1), Jan. 2007, 13-23.

* cited by examiner

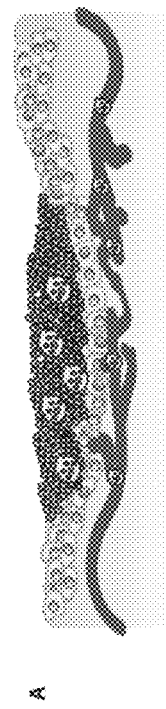
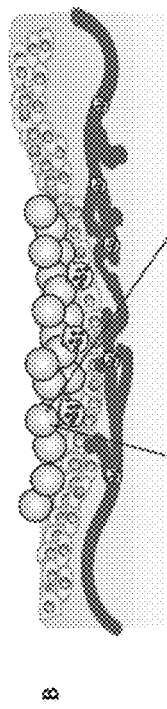
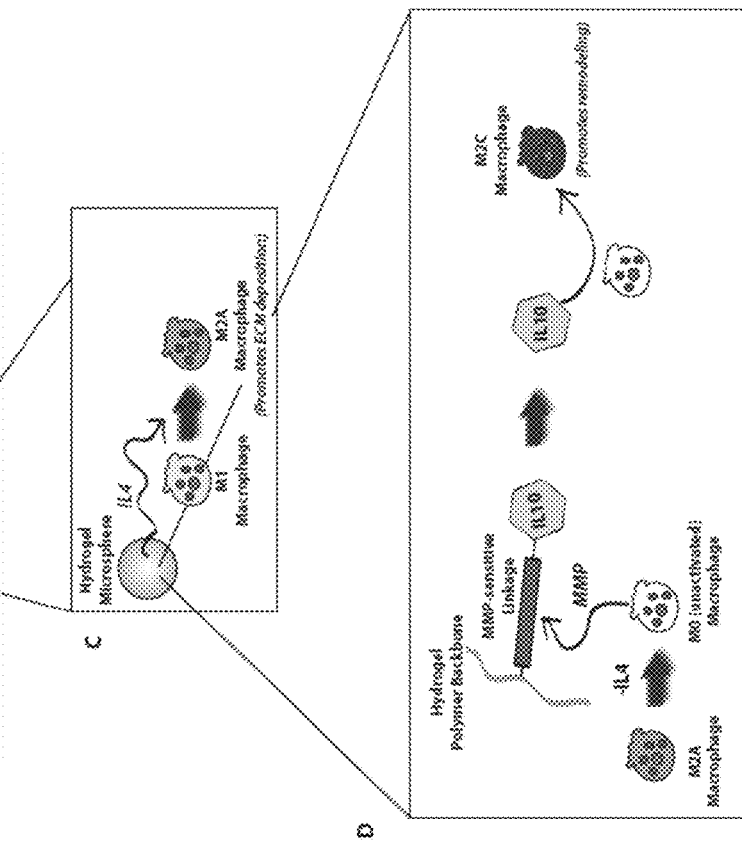
Figure 2A
Figure 2B
Figure 2C
Figure 2D

METHODS FOR INDUCING MACROPHAGE CONVERSION IN A WOUND

CROSS-REFERENCE TO RELATED APPLICATION

The present application is a divisional application under 35 U.S.C. § 121 of U.S. patent application Ser. No. 15/036,822, having a 35 U.S.C. § 371(c) completion date of May 16, 2016, which is a national phase entry under 35 U.S.C. § 371 of International Application No. PCT/US14/66517, filed Nov. 20, 2014, which is entitled to priority under 35 U.S.C. § 119(e) to U.S. Provisional Patent Application No. 61/906,630, filed Nov. 20, 2013. The contents of each of these applications are hereby incorporated by reference in its entirety herein.

BACKGROUND OF THE INVENTION

Normal wound healing involves three sequential phases: inflammation, proliferation/scar formation, and remodeling.

In chronic wounds, such as those that occur following severe tissue damage, or those that occur in patients with diabetes or chronic venous insufficiency, macrophages are stalled at the inflammation phase of healing (Acosta et al. Intl Wound J., 5: 530-539(2008), exhibiting an "M1" phenotype). The pro-inflammatory cytokines, reactive oxygen species, and danger signals released by these macrophages cause extensive damage to the tissue, resulting in wounds that fail to heal. However, the lingering presence of "M2A" macrophages, those that control the proliferative phase of healing, result in dense fibrous scarring. The macrophage population must further transition to the "M2C phenotype," to promote remodeling.

Hydrogels that inhibit the behavior of M1 macrophages via release of anti-inflammatory molecules are numerous (Repithel® from Munipharma, Germany, described in Beukelman et al. Burns, 34: 845-855 (2008)). However, anti-inflammatory technologies are known to inhibit wound healing (for example, Stadelmann 1998 American Journal of Surgery 176: 39S-47S) because inflammation is required for healing. Encapsulation of mesenchymal stem cells causes macrophage polarization to a M2-like phenotype (Hanson et al., Tissue Engineering Part A, 17: 2463-2471 (2011)).

However, none of these technologies promotes the natural wound healing sequence observed in healthy wound healing. Even technologies that could promote the release of macrophage-stimulating cytokines do not ensure that the proper cytokines are released after M2A macrophage behavior subsides, which is crucial to the wound healing process.

Therefore, a need exists in the art for improved methods for wound healing by promoting proper macrophage behavior.

SUMMARY OF THE INVENTION

As described below, the present invention includes methods and compositions for inducing macrophage conversion and promoting wound healing.

One aspect of the invention includes a method of inducing macrophage conversion in a wound comprising sequentially inducing conversion of a first population of wound macrophages in the wound to M2A macrophages and then converting a second population of wound macrophages in the wound to M2C macrophages, wherein inducing conversion of the macrophages comprises administering at least one agent from a delivery system to the macrophages.

Another aspect of the invention includes a method of sequentially inducing macrophage conversion in a wound comprising administering IL-4 from a delivery system to induce conversion of a first population of wound macrophages in the wound to M2A macrophages; and then administering IL-10 from the delivery system to induce conversion of a second population of wound macrophages in the wound to M2C macrophages.

Yet another aspect includes a method of preparing a hydrogel microsphere for wound healing comprising binding interleukin-10 (IL-10) to the hydrogel microsphere; exposing the hydrogel microsphere with bound IL-10 to interleukin-4 (IL-4); and displacing the bound IL-10 on an outer thickness of the hydrogel microsphere with IL-4, wherein the IL-4 binds to the hydrogel microsphere.

In another aspect, the invention includes a delivery system for sequentially inducing conversion of a first population of wound macrophages in a wound to M2A macrophages and a second population of wound macrophages to M2C macrophages comprising at least one agent selected from the group consisting of IL-4, an IL-4 agonist, a molecule that activates an IL-4 signaling pathway, IL-10, an IL-10 agonist, a molecule that activates an IL-10 signaling pathway, dexamethasone, a dexamethasone analog, and combinations thereof.

Still another aspect includes a hydrogel microsphere comprising an inner core of hydrogel polymers bound to interleukin-10 (IL-10) through an inner core binding molecule, wherein the IL-10 is bound to a first molecule that interacts with the inner core binding molecule; and an outer shell of hydrogel polymers bound to an outer shell binding molecule comprising interleukin-4 (IL-4) bound to a second molecule with a higher affinity to interact with the outer shell binding molecule than the IL-10 bound first molecule.

Yet another aspect includes a method of treating a chronic wound comprising administering to the wound at least one agent from a delivery system wherein the agent induces sequential conversion of a first population of wound macrophages in the wound to M2A macrophages and a second population of wound macrophages to M2C macrophages, wherein the sequential conversion of the wound macrophages promotes tissue remodeling.

Still yet another aspect of the invention includes a method of treating a chronic wound comprising exposing the wound to hydrogel microspheres, wherein the hydrogel microspheres comprise an inner core of hydrogel polymers bound to interleukin-10 (IL-10) and an outer shell of hydrogel polymers bound to interleukin-4 (IL-4).

In various embodiments of the above aspects or any other aspect of the invention delineated herein, the agent is selected from the group consisting of IL-4, an IL-4 agonist, a molecule that activates an IL-4 signaling pathway, IL-10, an IL-10 agonist, a molecule that activates an IL-10 signaling pathway, dexamethasone, a dexamethasone analog, and combinations thereof.

In one embodiment, the delivery system is a wound composition selected from the group consisting of a hydrocolloid composition, hydrogel, polysaccharide-based composition such as those comprising alginate or chitosan, semi-permeable polymeric adhesive film composition, foam composition, biological composition such as those comprising collagen, elastin, or hyaluronic acid, and polymeric scaffold. In another embodiment, the delivery system is selected from the group consisting of a sequential controlled-release delivery system such as an affinity-based delivery system, and a layer-by-layer delivery system. In yet another embodiment, the delivery system is a wound composition comprising hydrogel microspheres, such as hydrogel microspheres that comprise an inner core of hydrogel polymers bound to interleukin-10 (IL-10) and an outer shell of hydrogel polymers bound to interleukin-4 (IL-4). In another embodiment, the delivery system comprises hydrogel microspheres comprising an inner core of hydrogel polymers bound to interleukin-10 (IL-10) and an outer shell of hydrogel polymers bound to interleukin-4 (IL-4).

In such embodiments, inducing conversion comprises applying the hydrogel microspheres to the wound; inducing conversion of the first population of wound macrophages in the wound to M2A macrophages by exposure to IL-4 that is released from the outer shell of the hydrogel microspheres; and then inducing conversion of the second population of wound macrophages to M2C macrophages by exposure to IL-10 that is released from the inner core of the hydrogel microspheres. In some embodiments, the administering steps comprise applying hydrogel microspheres to the wound; sequentially exposing the first population of wound macrophages in the wound to IL-4 that is released from the outer shell, wherein the exposure of the first population of wound macrophages to the released IL-4 induces conversion to M2A macrophages; and then exposing the second population of wound macrophages to IL-10 that is released from the inner core, wherein exposure of the second population of wound macrophages to the released IL-10 induces conversion to M2C macrophages. In some embodiments, the delivery system comprises IL-4 bound to the hydrogel polymers through a binding molecule. In some embodiments, the binding molecule is non-covalently bound to the hydrogel polymers. In such embodiments, IL-4 is covalently bound to an affinity molecule that interacts with the binding molecule. In some more embodiments, IL-4 is released by dissociating the IL-4 from the binding molecule. In some embodiments, the delivery system comprises IL-10 bound to hydrogel polymers through a binding molecule. In such embodiments, IL-10 is bound to an affinity molecule that interacts with the binding molecule, wherein the binding molecule is bound to the hydrogel polymers. In some more embodiments, the affinity molecule is non-covalently bound to the hydrogel polymers. In yet more embodiments, the bound IL-10 is released by enzymatic cleavage by an enzyme that is present in the wound, such as a secreting enzyme comprising a matrix metalloprotease that cleaves the bound IL-10 from the polymer.

In another embodiment, binding IL-4 to the hydrogel microsphere comprises binding IL-4 to the hydrogel microsphere. In yet another embodiment, binding IL-4 to the hydrogel microsphere comprises binding IL-4 to a binding molecule bound to the hydrogel microsphere. In such an embodiment, binding IL-4 to the binding molecule comprises binding IL-4 to an affinity molecule that interacts with the binding molecule bound to the hydrogel microsphere.

In another embodiment, binding IL-10 to the hydrogel microsphere comprises binding IL-10 to the hydrogel microsphere. In yet another embodiment, binding IL-10 to the hydrogel microsphere comprises binding IL-10 to a binding molecule bound to the hydrogel microsphere. In such an embodiment, binding IL-10 to the binding molecule comprises binding IL-10 to an affinity molecule that interacts with the binding molecule bound to the hydrogel microsphere. In still another embodiment, binding IL-10 to the hydrogel microsphere comprises binding IL-10 to the hydrogel microsphere through a matrix metalloproteinase (MMP) sensitive peptide. In yet another embodiment, binding IL-10 to the hydrogel microsphere comprises binding IL-10 through a matrix metalloprotease (MMP) sensitive peptide to an affinity molecule that interacts with avidin, wherein avidin is bound to the hydrogel microsphere. In such an embodiment, exposing the hydrogel microsphere to IL-4 comprises exposing the hydrogel to IL-4 covalently bound to a higher affinity molecule, wherein the higher affinity molecule interacts with avidin and has a higher association constant and/or lower dissociation constant than the affinity molecule bound to IL-10.

In another embodiment, IL-10 is covalently bound to the first molecule through a peptide linker, such as comprising a matrix metalloproteinase cleavage sequence. In yet another embodiment, the inner core binding molecule and outer shell binding molecule are avidin. In still another embodiment, the first molecule bound to IL-10 is 4'-hydroxyazobenzene-2-carboxylic acid (HABA). In yet another embodiment, the higher affinity second molecule bound to IL-4 is biotin. It still another embodiment, IL-4 is covalently bound to the higher affinity second molecule.

In various other embodiments of the above aspects or any other aspect of the invention delineated herein, treating a chronic wound further comprising sequentially converting a first population of wound macrophages in the wound to M2A macrophages by exposing the first population of wound macrophages to IL-4 and converting a second population of wound macrophages to M2C macrophages by exposing the second population of wound macrophages to IL-10.

BRIEF DESCRIPTION OF THE DRAWINGS

FIG. 2A is a schematic illustrating the control over macrophage behavior in a chronic wound, with resulting effects on the wound healing process. M1 macrophages are present in high numbers in chronic wounds.

FIG. 2B is a schematic illustrating the flowable slurry of hydrogel microspheres is used to fill the wound.

FIG. 2C is a schematic illustrating that the microspheres first release M2A-promoting cytokines such as IL-4, which converts any macrophages in the vicinity into M2A macrophages that in return promote synthesis of extracellular matrix (ECM) and tissue repair.

FIG. 2D is a schematic illustrating when the supply of M2A-promoting cytokine such as IL-4 is exhausted, M2A macrophages revert to an unactivated phenotype and/or are replaced by newly arriving unactivated macrophages, which have heightened ability to degrade MMP-sensitive molecules compared to M2A macrophages. Therefore, an M2C-promoting cytokine such as IL-10, which is conjugated to the hydrogel via an MMP-sensitive linkage, cannot be released until the M2A population subsides, which occurs when there is no more M2A-promoting cytokine in the system. Thus, a M2C-promoting cytokine is released after M2A-promoting cytokine, which causes the conversion of any macrophages in the vicinity to convert to an M2C phenotype after a period of time that M2A macrophages dominate. The M2C macrophages promote remodeling of the tissue and finish the wound healing process. Note that this process would work for any molecule besides IL-4 that promotes the M2A phenotype and any molecule besides IL-10 that promotes the M2C phenotype.

$$[IL4-\text{avidin conjugate}] \underset{K_r}{\overset{K_f}{\rightleftharpoons}} [\text{free } IL4] + [\text{immobilized avidin}]$$

which yields

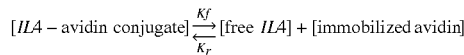

as the dissociation constant of the IL-4-avidin complex. Since IL-4 is loaded primarily at the surface of the hydrogel spheres, only the forward reaction occurs, and release of IL-4 is controlled by $K_f$ and the loading of IL-4:

$$\frac{\partial [IL4]}{\partial t} = -K_f[IL4-\text{avidin conjugate}].$$

Other parameters that control IL-4 release include the crosslinking density of the hydrogels, the amount of avidin conjugated to the polymer backbone, the amount of biotin conjugated to each molecule of IL-4, and the total amount of IL-4 loaded into the system.

Figure 5:
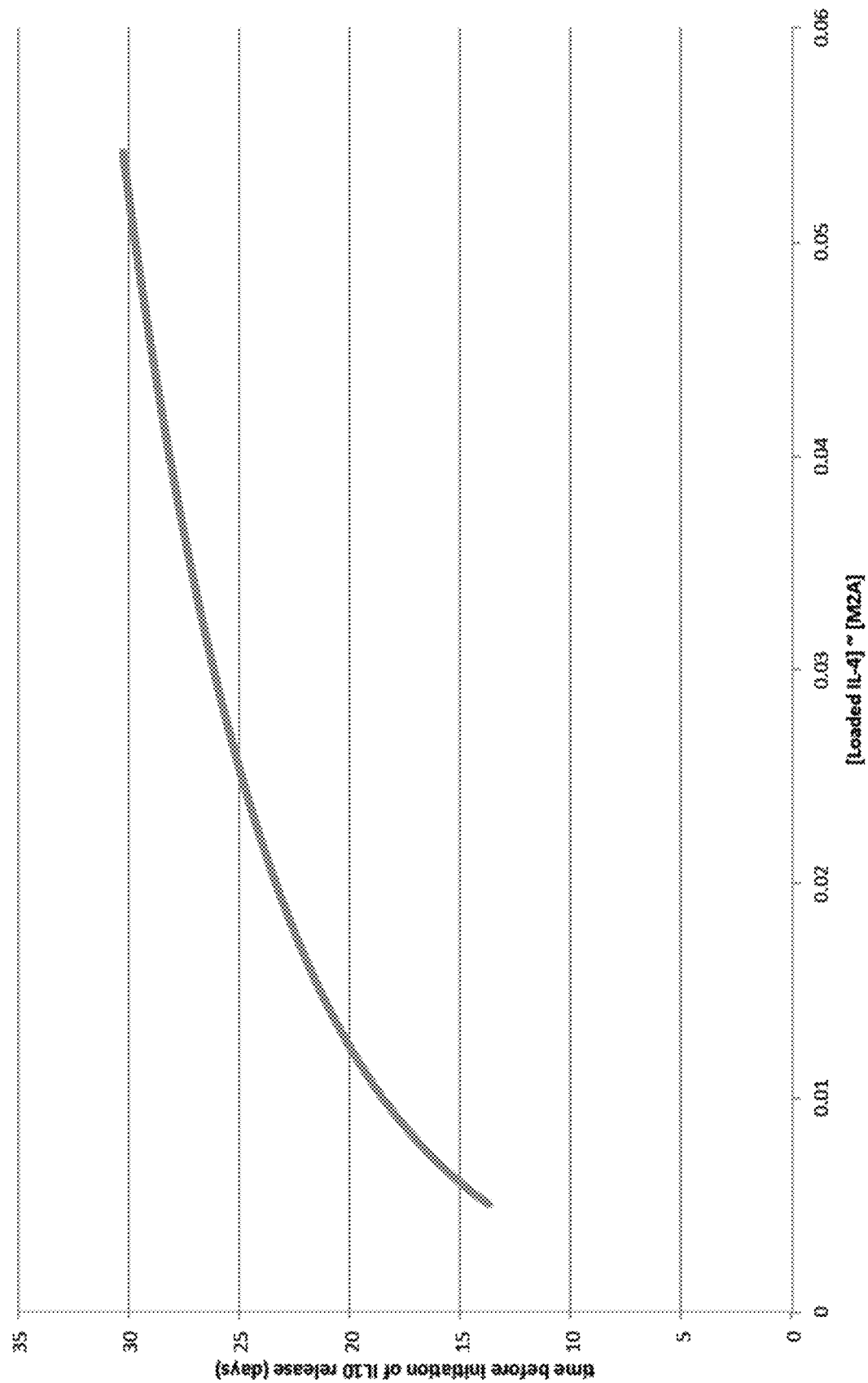

FIG. 5 demonstrates how delayed release of IL-10 is achieved via control over macrophage phenotype. Because M2A macrophages have reduced ability to degrade MMP-sensitive moieties, the release of IL-10 can only begin when the supply of IL-4 is exhausted and the macrophage population assumes an unactivated phenotype that can degrade MMP-sensitive moieties. Thus, control over the amount of time of the delay before IL-10 is released is controlled by varying the timing of the presence of M2A macrophages, which is controlled via IL-4 release.

Figure 6:
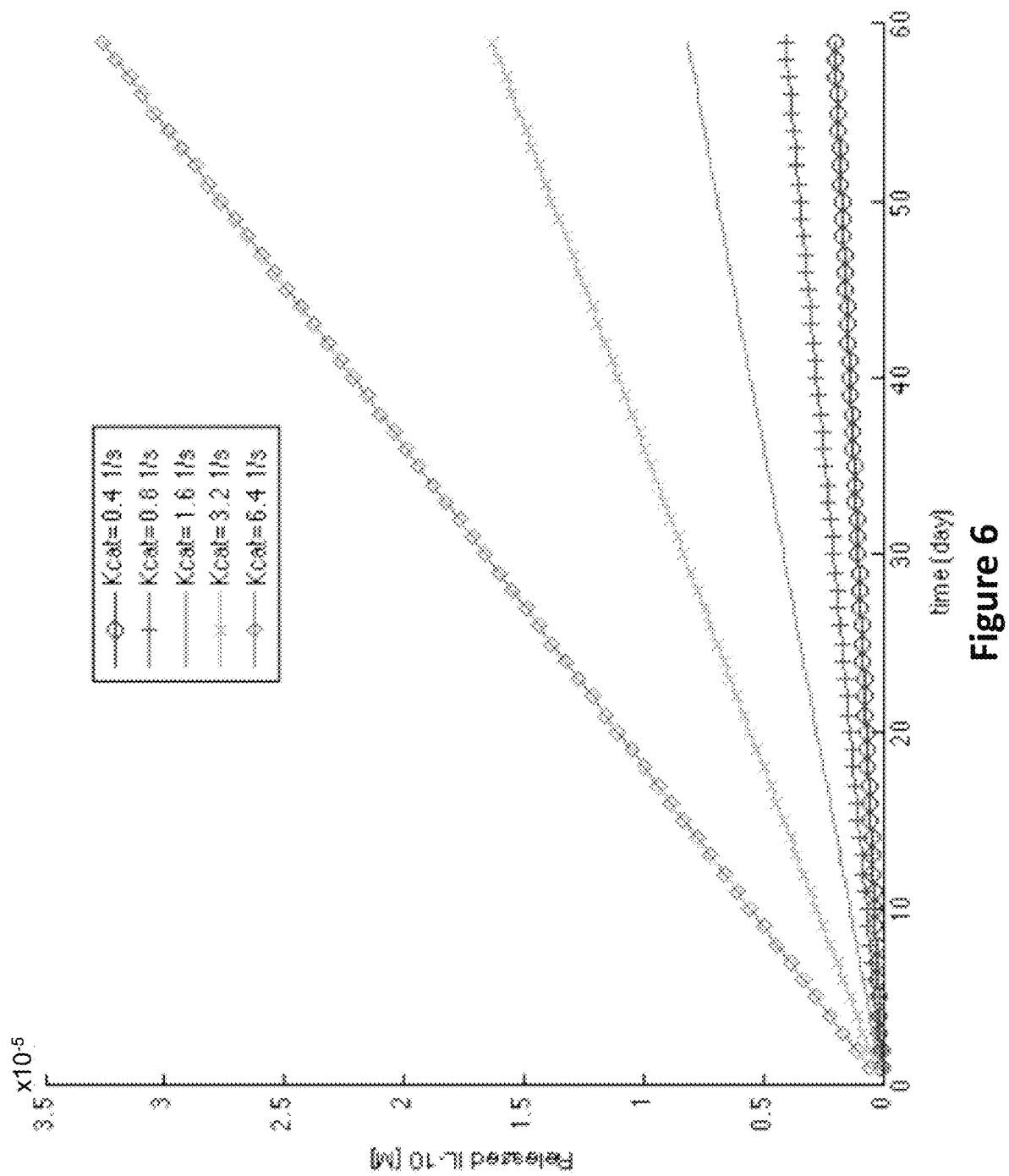

FIG. 6 demonstrates that the rate of IL-10 release can be controlled by varying the sequence of the MMP-sensitive peptide linkage to change the ability of MMPs to degrade it (Kcat). Then, release of IL-10 follows Michaelis-Menten kinetics. However, because the concentration of MMP-sensitive linkages within the hydrogel is much higher than $K_m$ (the substrate concentration needed to achieve a half-maximum enzyme reaction rate) and would saturate the enzyme, release of IL-10 is governed by $$\frac{\partial [IL10]}{\partial t} = -K_{cat}[MMP].$$

The release profile of IL-10 can also be controlled by varying the crosslinking density of the hydrogels or the amount of IL-10 conjugated to the polymer backbone via the MMP-sensitive linkage. In addition, the daily dose of IL-10 will affect the rate of release, since greater activation of M2C macrophages will lead to higher levels of MMP9 secretion and faster rates of cleavage of the MMP-sensitive linkages.

Figure 7:
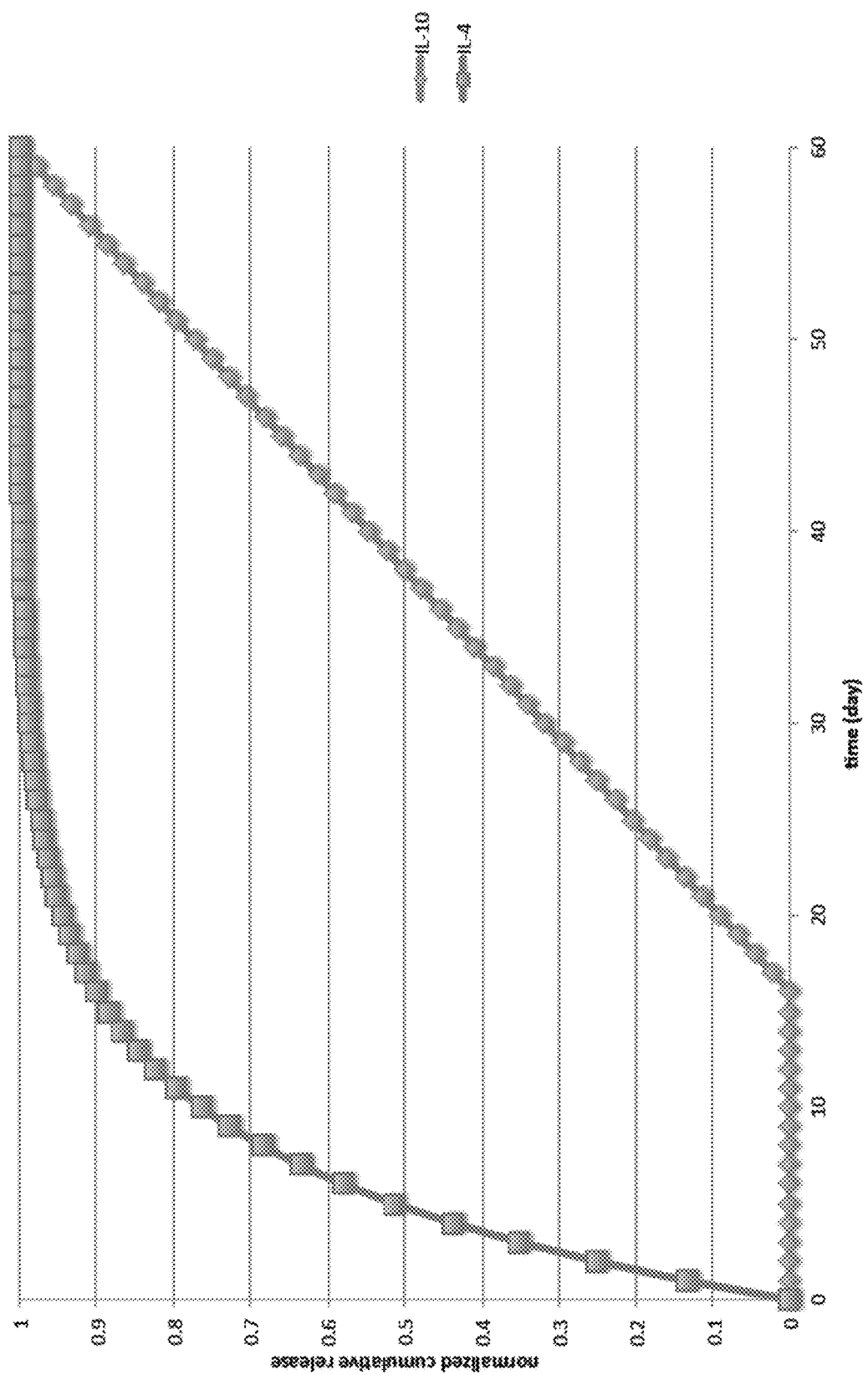

FIG. 7 shows that sequential release of IL-4 and IL-10 can be achieved using this technology, thus causing sequential activation of M2A and M2C phenotypes, and sequential phases of proliferation and remodeling.

Figure 8:
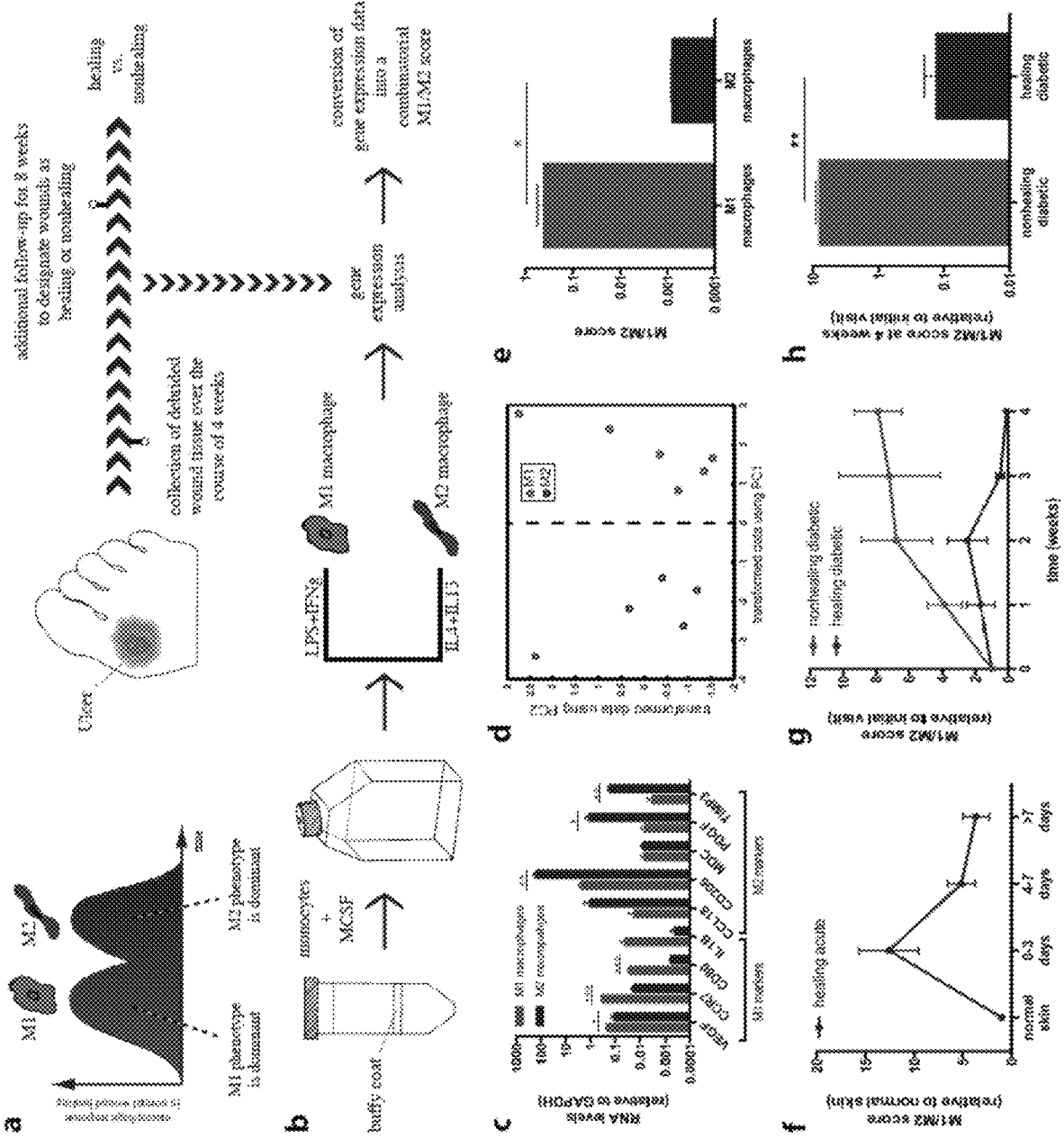

FIG. 8 is a panel of images showing the conversion of macrophage markers into a single combinatorial score that describes the expression profile of macrophage markers in human healing and nonhealing diabetic ulcers.

Figure 9:
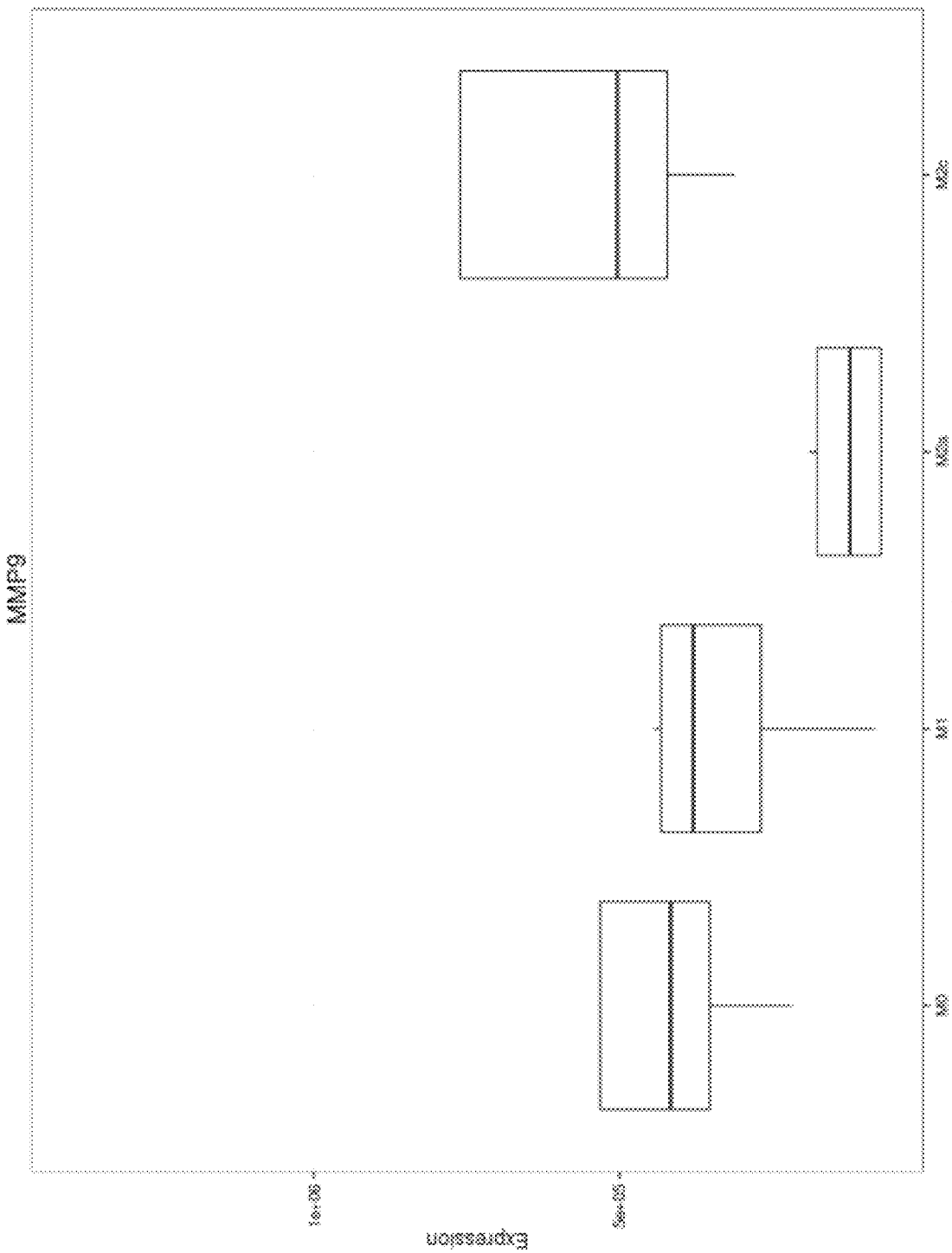

FIG. 9 shows the higher expression of Matrix Metalloprotease 9 (MMP9) in M2C macrophages identified by RNA-seq, suggesting a role in the remodeling stage of the wound healing process.

Figure 10:
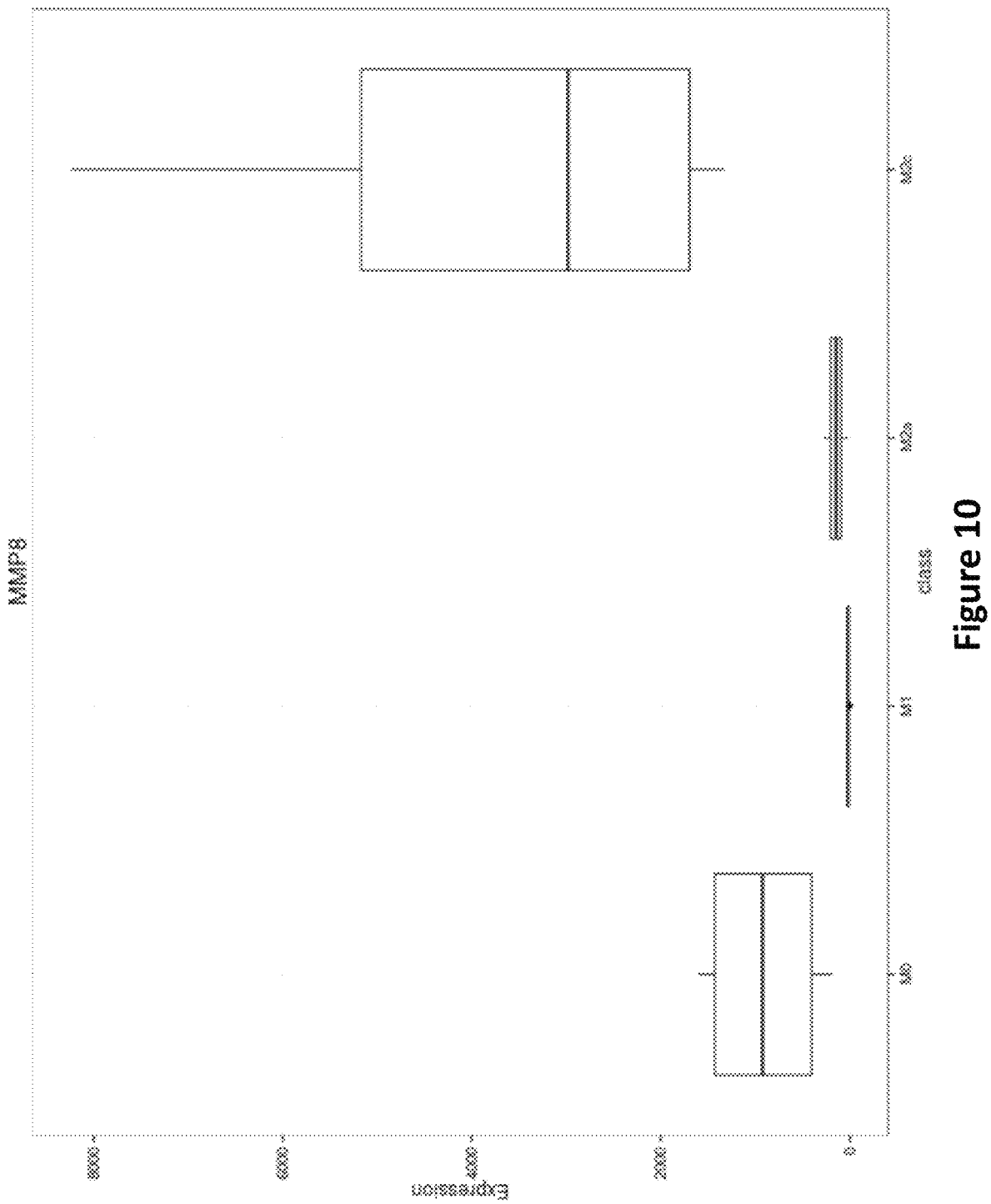

FIG. 10 shows higher expression of Matrix Metalloprotease 8 (MMP8) in M2C macrophages identified by RNA-seq, suggestive of their role in the remodeling stage of the wound healing process.

Figure 11:
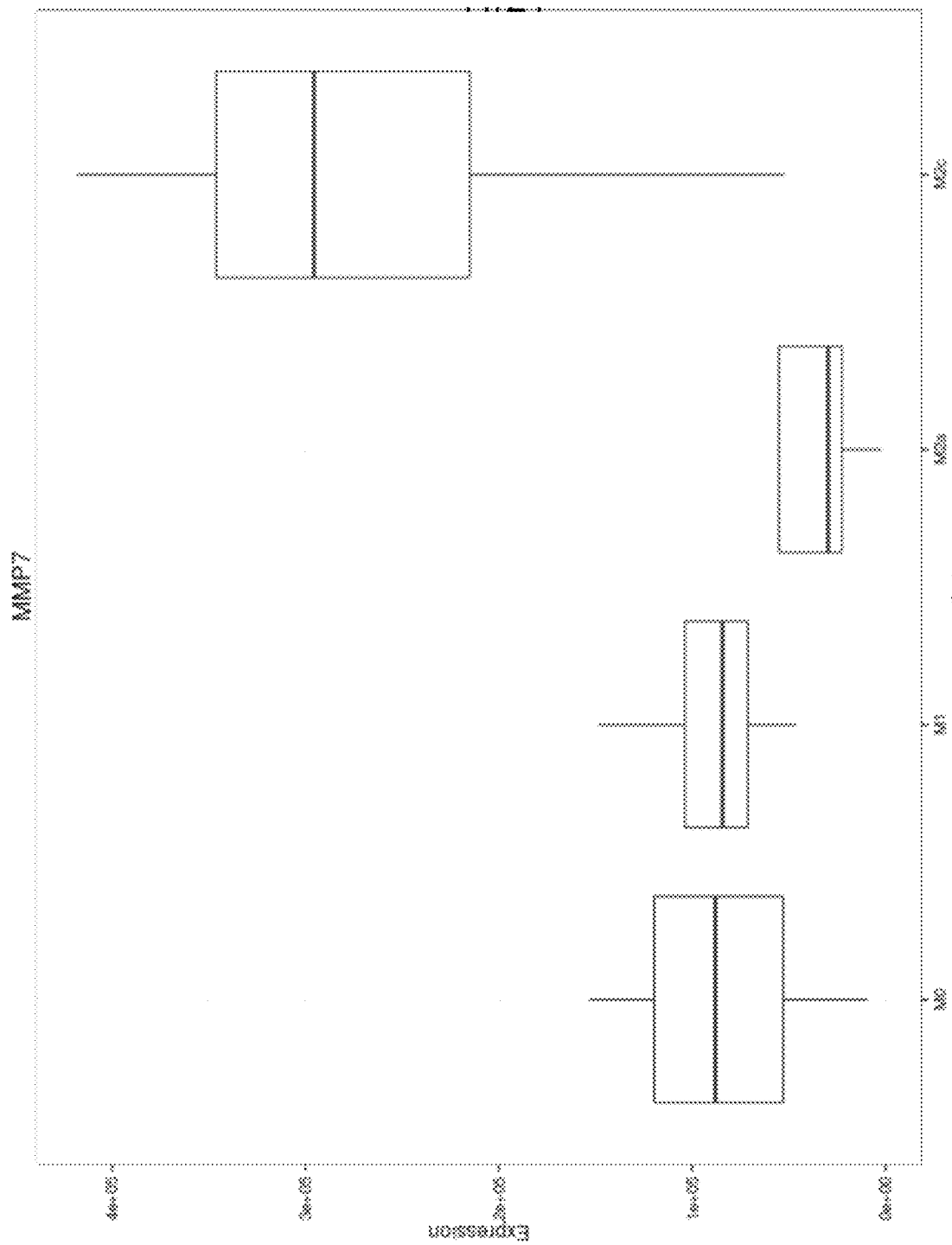

FIG. 11 shows higher expression of Matrix Metalloprotease 7 (MMP7) in M2c macrophages identified by RNA-seq, suggestive of their role in the remodeling stage of the wound healing process.

Figure 12:
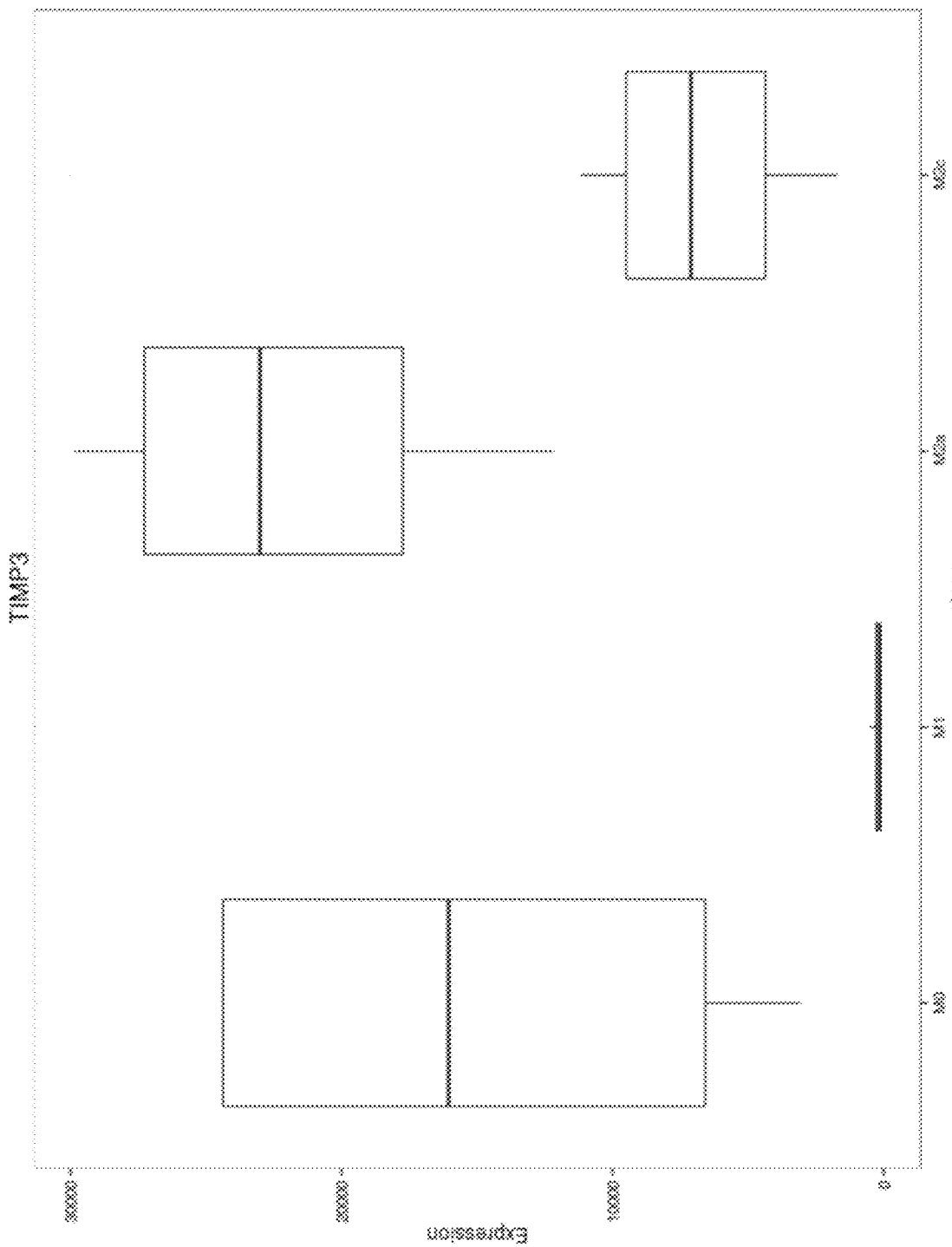

FIG. 12 shows higher expression of Metalloproteinase inhibitor 3 (TIMP3) in M2a macrophages identified by RNA-seq, suggestive of their role in earlier stages of the wound healing process.

Figure 13:
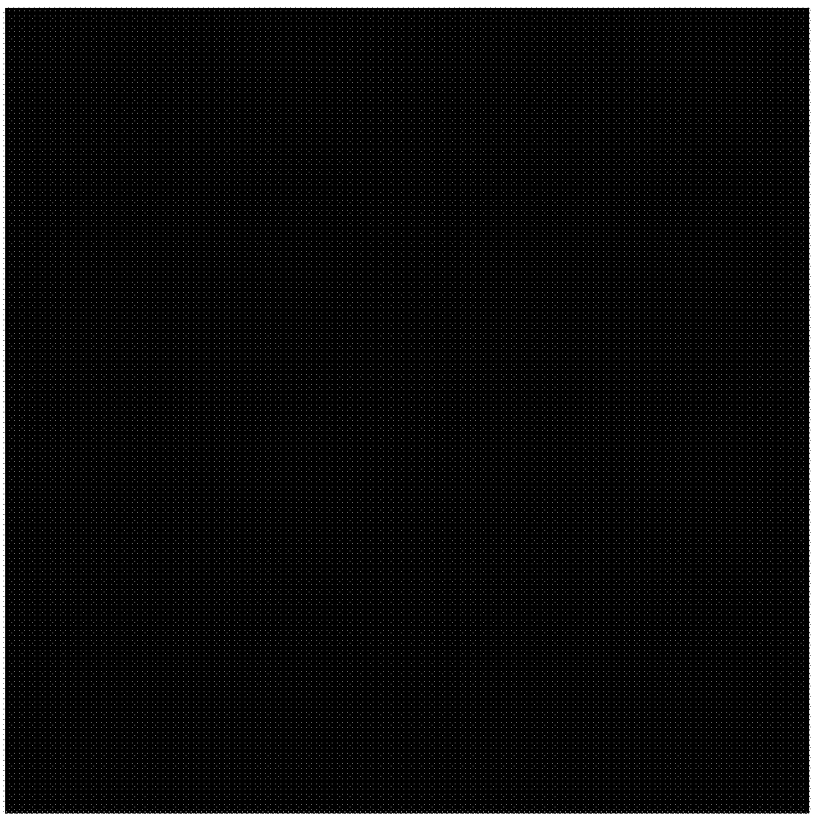
Figure 13:
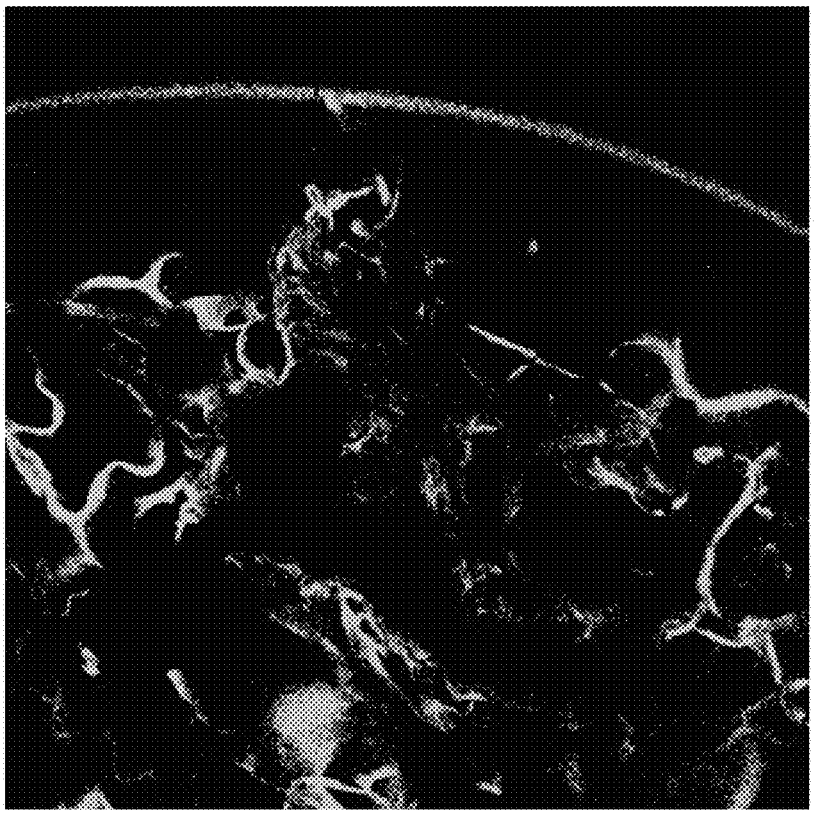

FIG. 13 is a panel of images showing that selective binding of streptavidin Dylight 594 to biotinylated collagen scaffolds was observed, but not to nonbiotinylated scaffolds.

Figure 14:
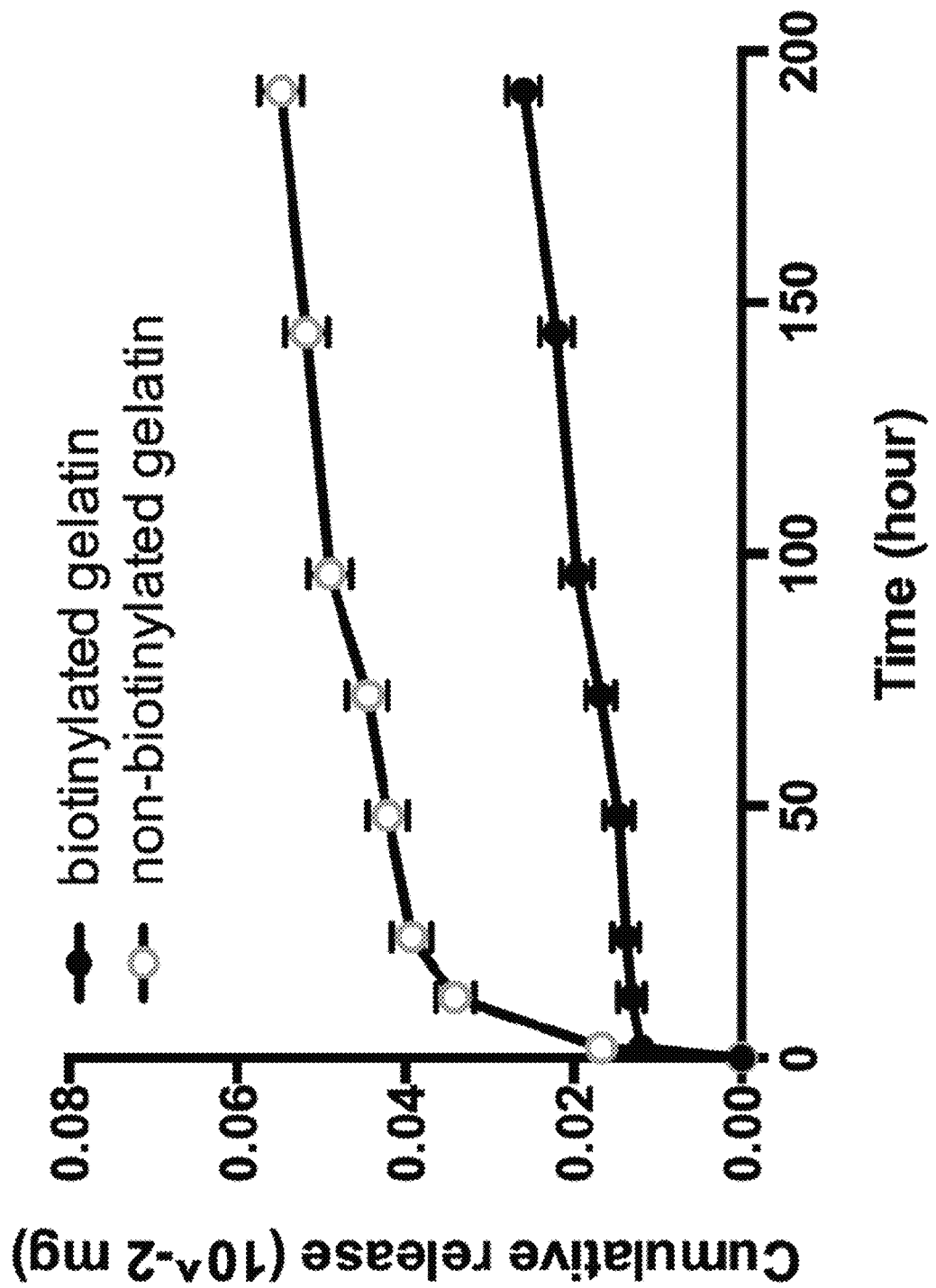

FIG. 14 is a graph showing release of streptavidin Dylight 594 from biotinylated vs nonbiotinylated gelatin disks (10% wt). Biotinylation cause delayed release of streptavidin from gelatin disks.

Figure 15:
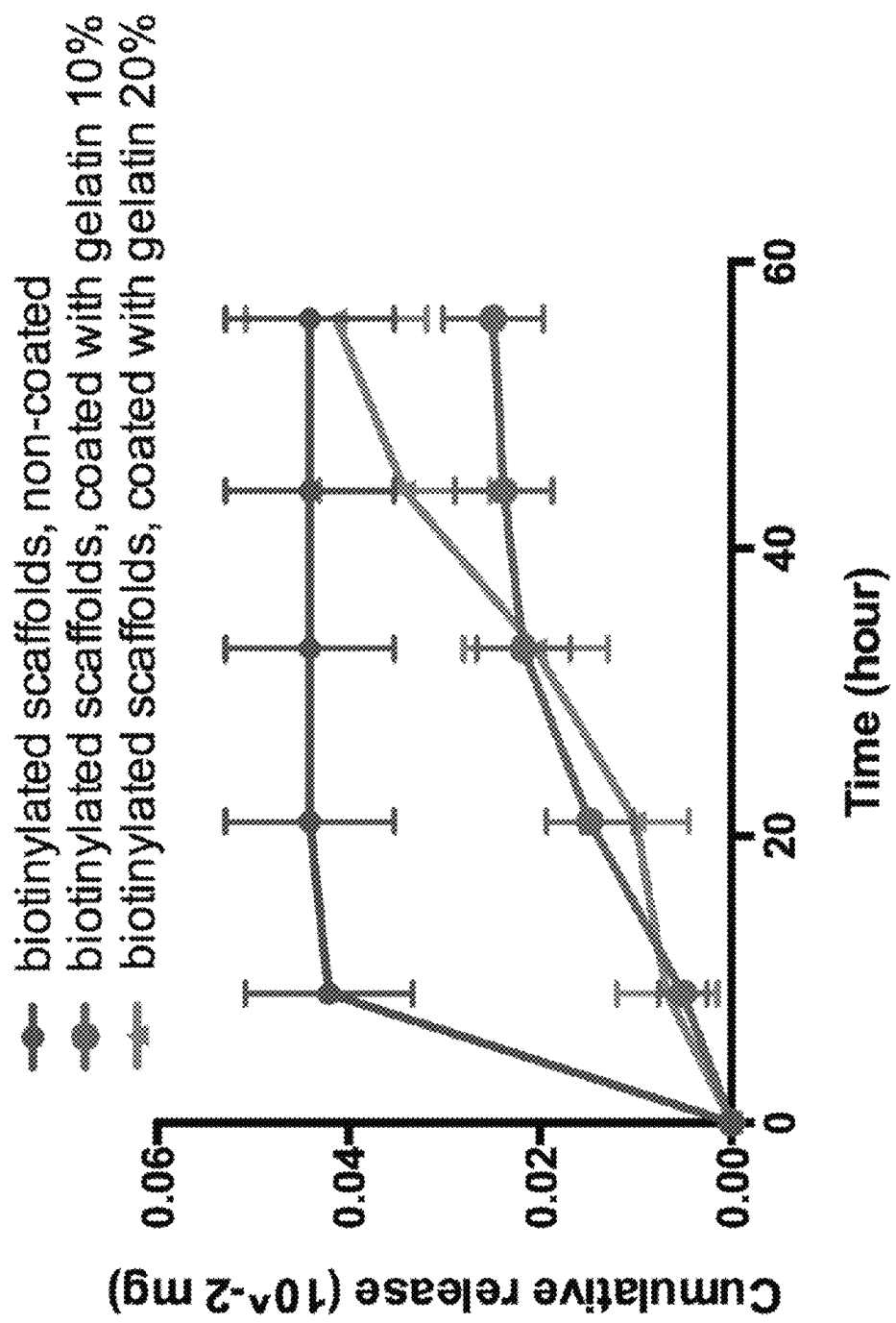

FIG. 15 is a graph showing release of streptavidin Dylight 594 from biotinylated collagen scaffolds, and from biotinylated scaffolds that have been coated with 10 or 20 wt % gelatin.

Figure 16:
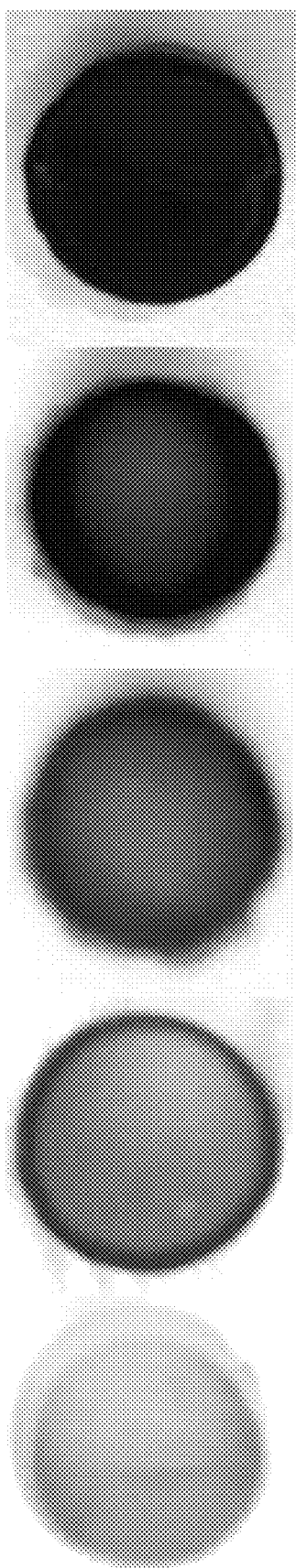

FIG. 16 is a panel of images that show that diffusion into hydrogels can be used to control the thickness of the shell/core.

Figure 17:
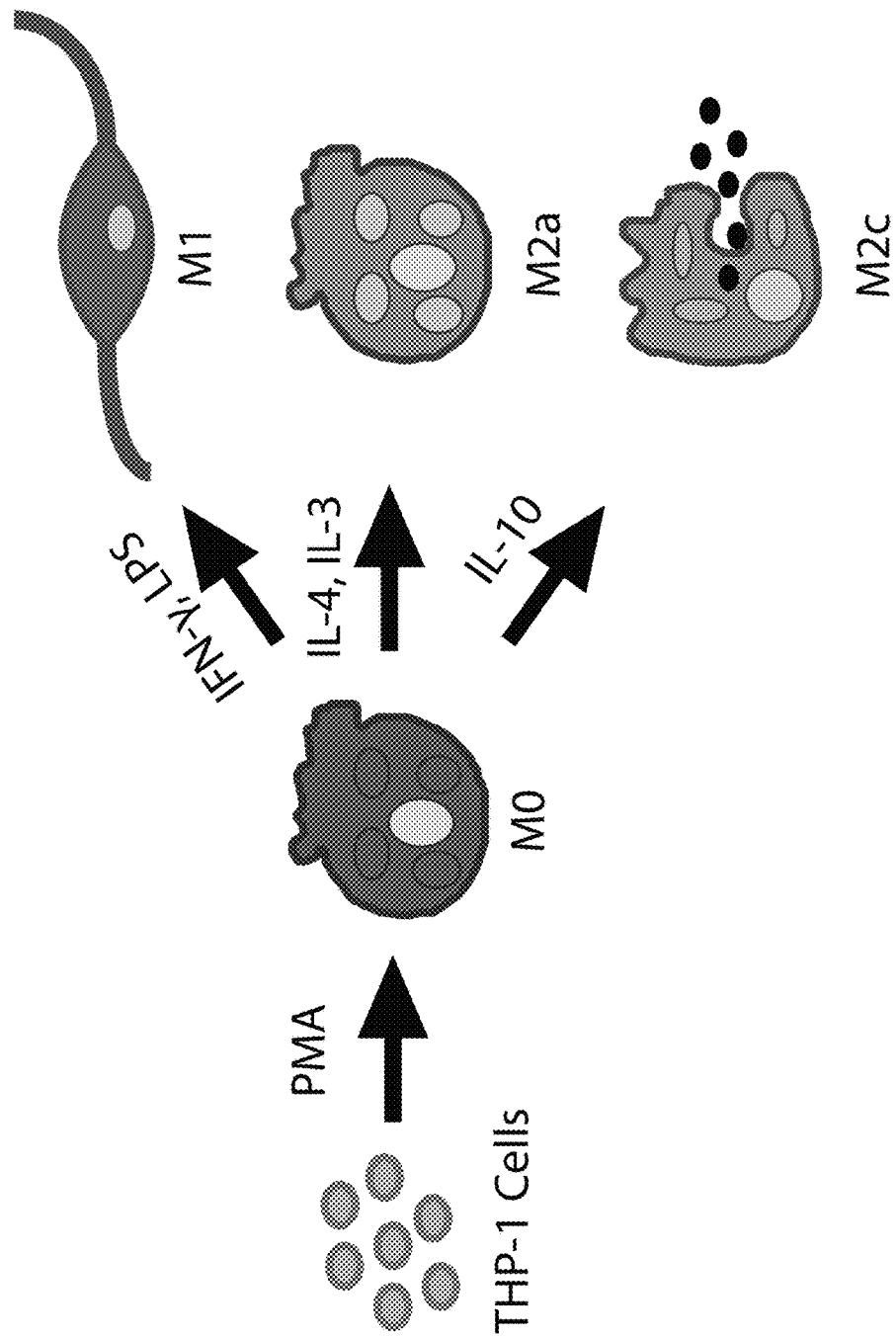

FIG. 17 is an illustration showing the conversion of macrophages.

Figure 18:
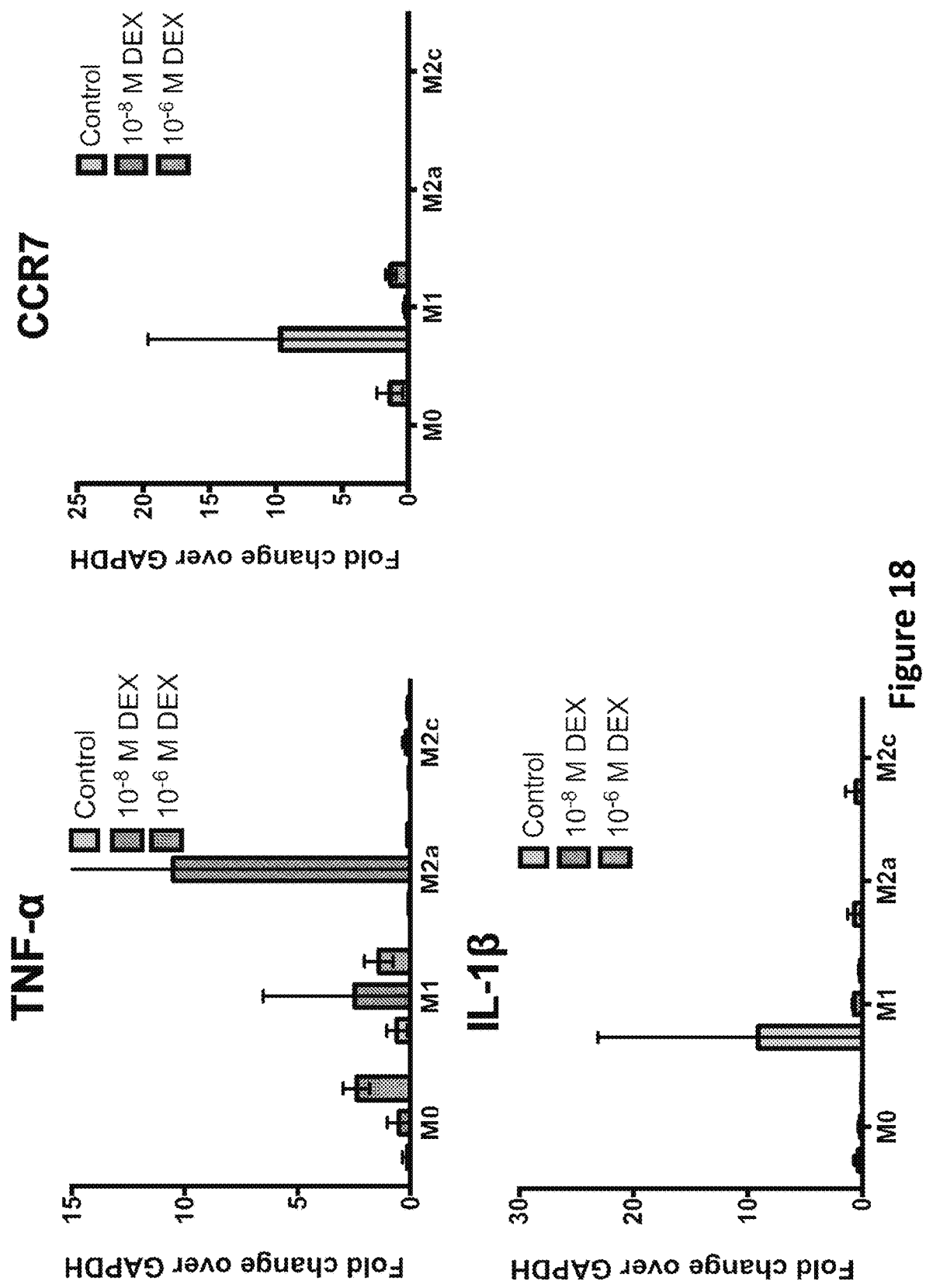

FIG. 18 is a panel of graphs showing expression of M1 macrophage markers in macrophages of M0, M1, M2A or M2C phenotypes that have been treated with dexamethasone.

Figure 19:
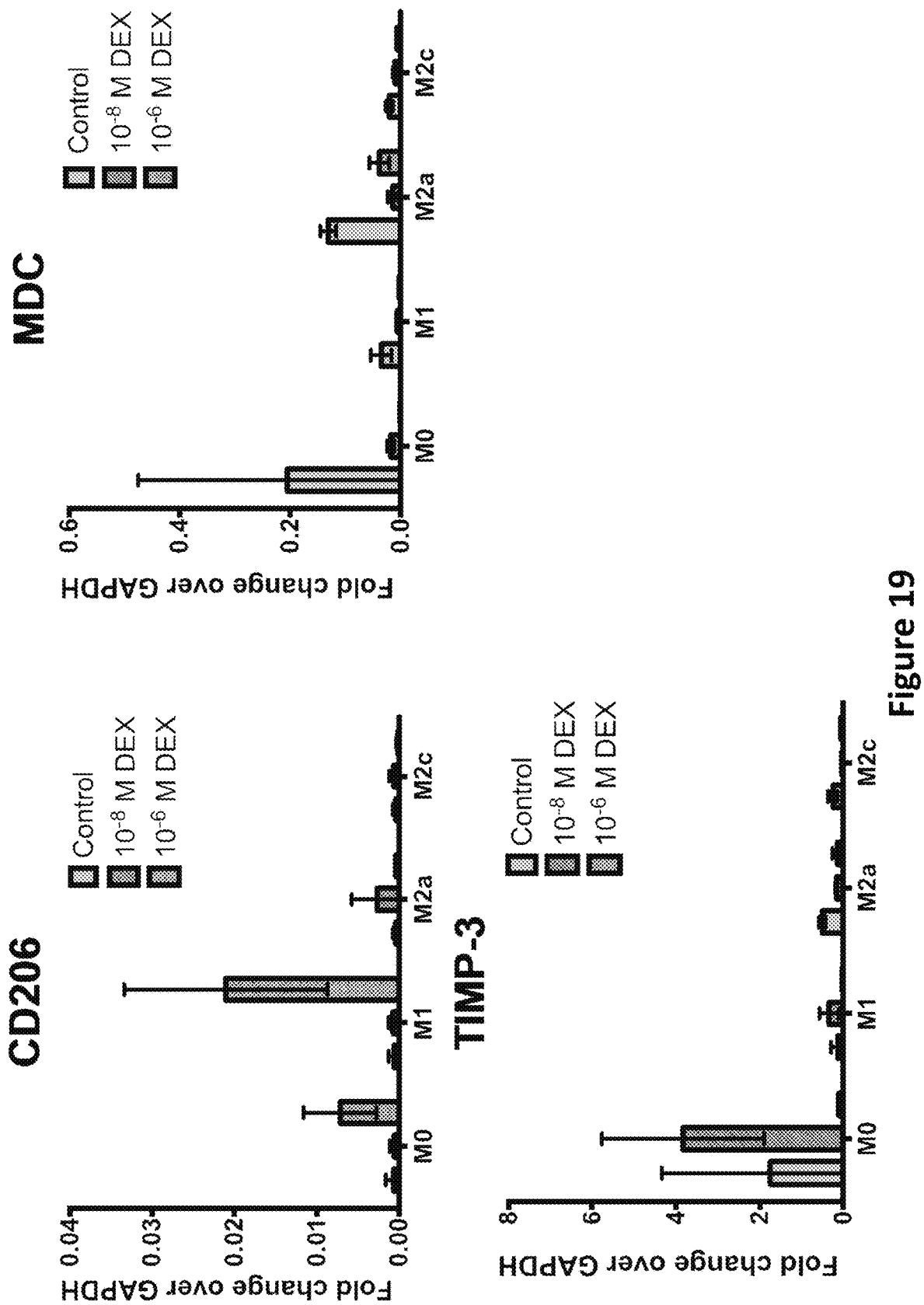

FIG. 19 is a panel of graphs showing expression of M2A macrophage markers in macrophages of M0, M1, M2A or M2C phenotypes that have been treated with dexamethasone.

Figure 20:
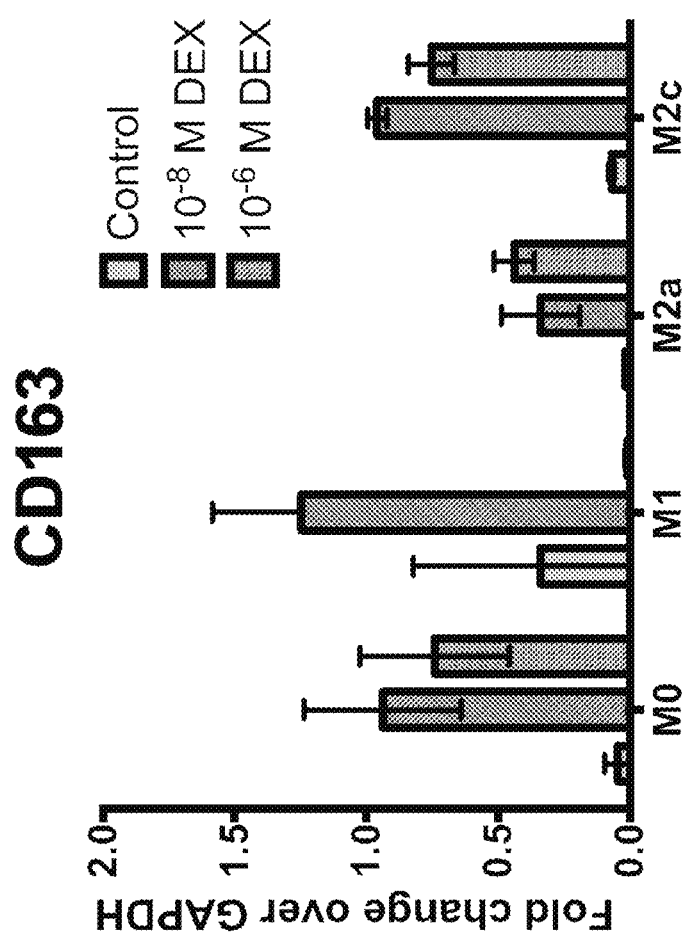

FIG. 20 is a graph showing expression of the M2C macrophage marker CD163 in macrophages of M0, M1, M2A or M2C phenotypes that have been treated with dexamethasone, which shows that the addition of dexamethasone to macrophages of all four phenotypes caused their conversion to the M2C phenotype.

Figure 21:
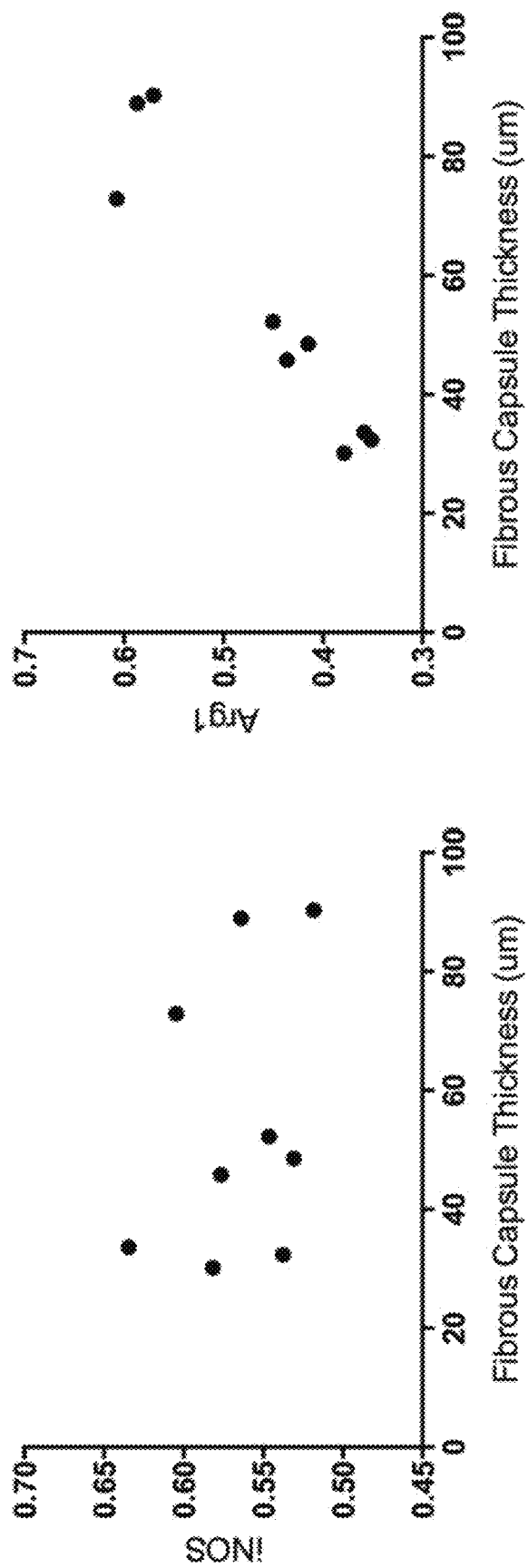

FIG. 21 is a panel of graphs showing a correlation analysis of relationships between macrophage phenotype and the fibrous capsule formation, a model of fibrosis, surrounding model biomaterials implanted subcutaneously in mice for 3 days to 3 weeks. Results showed that M1 macrophages (as indicated by iNOS expression) were not correlated with fibrosis, while M2 macrophages (as indicated by Arg1 expression) were highly correlated with fibrosis (Pearson's correlation coefficient of 0.948).

DETAILED DESCRIPTION OF THE INVENTION

Definitions

Unless defined otherwise, all technical and scientific terms used herein have the same meaning as commonly understood by one of ordinary skill in the art to which the invention pertains. Although any methods and materials similar or equivalent to those described herein may be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

As used herein, the articles "a" and "an" are used to refer to one or to more than one (i.e., to at least one) of the grammatical object of the article. By way of example, "an element" means one element or more than one element.

As used herein when referring to a measurable value such as an amount, a temporal duration, and the like, the term "about" is meant to encompass variations of ±20% or within 10%, 9%, 8%, 7%, 6%, 5%, 4%, 3%, 2%, 1%, 0.5%, 0.1%, 0.05%, or 0.01% of the specified value, as such variations are appropriate to perform the disclosed methods. Unless otherwise clear from context, all numerical values provided herein are modified by the term about.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

An "affinity molecule" refers to a molecule that may bind, either covalently or non-covalently, to another molecule, such as a binding molecule, with selective high affinity or selective intermolecular forces. The affinity molecule may be attached to a polymer or protein and still interact with its binding molecule. The affinity molecule pairs with the binding molecule such that interaction of the affinity molecule with the binding molecule allows exposure of wound macrophages to an agent that induces macrophage conversion, such as M0 and/or M1 wound macrophages to M2A macrophages or M2A and/or other wound macrophages to M2C macrophages. In some embodiments, the affinity molecule includes biotin, 4'-hydroxyazobenzene-2-carboxylic acid (HABA), and other avidin binding molecules, an antibody from an antibody/antigen pair, a heparin-binding protein, a receptor, ligand binding domain from a receptor, and other affinity molecule from an affinity-based system.

The terms "binding," "bind," "bound" refer to an interaction between two molecules. The interaction may include a covalent or non-covalent bond. The interaction may also be reversible or irreversible depending on the type of interaction, such as covalent bond formation.

A "binding molecule" refers to a molecule that may bind, either covalently or non-covalently, to another molecule, such as an affinity molecule, with selective high affinity or selective intermolecular forces. Like the affinity molecule, the binding molecule may be attached to a polymer or protein and interact with its affinity molecule. The binding molecule pairs with the affinity molecule such that interaction of the binding molecule affinity molecule with the affinity molecule allows exposure of wound macrophage to an agent that induces macrophage conversion, such as M0 and/or M1 wound macrophages to M2A macrophages or M2A and/or other wound macrophages to M2C macrophages. Examples of binding molecules may include, but are not limited to, avidin, avidin-like polymers such as NeutrAvidin®, CaptAvidin® and streptavidin, tamavidins, other biotin binding proteins, an antigen from an antibody/antigen pair, heparin, ligand, and other molecule from an affinity-based system.

The terms "agent" or "agent inducing macrophage conversion" refers to one or more molecules that when wound macrophages induces conversion to M2A and/or conversion to M2C.

The term "IL-4 agonist" refers to a molecule that binds the IL-4 receptor and activates IL-4 receptor signaling.

The term "IL-10 agonist" refers to a molecule that binds the IL-10 receptor and activates IL-10 receptor signaling.

The phrase "a molecule that activates an IL-4 signaling pathway" as used herein, refers to a molecule, such as an activated IL-4 receptor or fragment thereof, or other molecule that activates IL-4 signaling or feeds into and activates an IL-4 receptor signaling. Examples may include, but are not limited to, an IL-4 antagonist, an activated IL-4 receptor signaling domain, an activated IL-4 receptor, and derivates thereof.

The phrase "a molecule that activates an IL-10 signaling pathway" as used herein, refers to a molecule, such as an activated IL-10 receptor or fragment thereof, or other molecule that activates IL-10 signaling or feeds into and activates an IL-10 receptor signaling. Examples may include, but are not limited to, an IL-10 antagonist, an activated IL-10 receptor signaling domain, an activated IL-10 receptor, and derivates thereof.

The terms "conversion," and "converting" refer to the change in macrophage phenotype or subtype from one macrophage phenotype or subtype to another macrophage phenotype or subtype.

By "delivery system" is meant an artificial device that allows administration of an agent to a target site, such as a wound. The delivery system may be implantable in the subject or it may be an external system to deliver the agent. When implantable, the delivery system is biocompatible. The delivery system may also be biodegradable, with a biodegradable rate that is compatible with the rate of delivery of the agent(s) or exposure of the target site to the agent. In one embodiment, the delivery system is sequential controlled-release delivery system, layer-by-layer delivery system, microspheres, or wound composition.

By "effective amount" is meant the amount required to reduce or improve at least one symptom related to the wound relative to an untreated patient. The effective amount of an active compound(s) used for therapeutic treatment of a chronic wound varies depending upon the manner of administration, the age, body weight, and general health of the subject.

The phrase "enzyme that is present in the wound" refers to an enzyme secreted by any cells in a wound including but not limited to any subtype or phenotype of macrophage described herein.

"Hydrogel microsphere," "hydrogel microspheres" and "microspheres" as used herein refer to a three dimensional structure on the order of about 1 to about 999 microns made of polymers, such as natural polymers, synthetic polymers, or combinations of both, and liquid, such as water.

"Hydrogel polymers" as used herein refer to natural polymers, synthetic polymers or combinations of both. Natural polymers can include polymers such as anionic polymers (for example, hyaluronic acid, alginic acid, pectin, carrageenan, chondroitin sulfate, dextran sulfate), cationic polymers (for example, chitosan and polylysine), amphipathic polymers (such as collagen, gelatin, carboxymethyl chitin and fibrin) and neutral polymers (for example, dextran, agarose and pullulan), and their derivatives or neutral polymers known in the art. Synthetic polymer hydrogels include, but are not limited to, polymers such as polyesters, poly(ethylene glycol), poly(lactic acid), poly(lactic-co-glycolic acid), polycaprolactone, poly(hydroxyl butyrate); poly(propylene fumerate-co-ethylene glycol)±acrylate end groups, poly(poly(ethylene glycol)/poly(butylene oxide)terephthalate), and any derivatives thereof or known in the art. Synthetic polymer hydrogels may include, for example, other polymers such as: poly(ethylene glycol)-bis-(poly(lactic acid)-acrylate); poly(ethylene glycol)±cyclodextrins; poly(ethylene glycol)-g-poly(acrylamide-co-Vamine); polyacrylamide; poly(N-isopropyl acrylamide-co-acrylic acid); poly(N-isopropyl acrylamide-co-ethyl methacrylate); poly(vinyl acetate)/poly(vinyl alcohol); poly(N-vinyl pyrrolidone); poly(methyl methacrylate-co-hydroxyethyl methacrylate); polyacrylonitrile-co-allyl sulfonate); poly(biscarboxy-phenoxy-phosphazene); poly(glucosylethyl methacrylate-sulfate), and derivatives thereof or synthetic polymers known in the art. Combinations of natural and synthetic polymers may include polymers such as poly (polyethylene glycol-co-peptides), alginate g-(polyethylene oxide-polypropylene oxide-polyethylene oxide), poly(polylactic-co-glycolic acid-co-serine), collagen-acrylate, alginate-acrylate, poly(hydroxyethly methacyrlate-g-peptide), poly(hydroxyethyl methacyrlate/collagen), hyaluronic acid-g-N-isopropyl acrylamide), or any combination of natural and synthetic polymers described here or known in the art.

The term "polymeric scaffold" as used herein refers to a biocompatible material that may comprise natural or synthetic polymers or a combination thereof. The polymeric scaffold may be shaped or formed to conform with the wound. The polymeric scaffold may include one or more macrophage conversion agent(s).

The terms "induce," and "induction" refer to the promoting a change in macrophage phenotype from one macrophage subtype to another macrophage subtype.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified. "Purified" can also refer to a molecule separated after a bioconjugation technique from those molecules which were not efficiently conjugated.

The phrase "layer-by-layer delivery system" refers to a composition with multiple layers. Each layer may include one or more agents. The composition may be biocompatible and biodegradable. The thickness of the layers, degradation rate of the layer, components in the composition, affinity of the agent for the target site, affinity of the agent for the composition components, the concentration of agent within the layer, and the rate of diffusion of the agent may influence the release of the agent.

The phrase "macrophage conversion" as used herein refers to the sequential change in macrophage phenotype. For example, transitioning macrophage from pro-inflammatory (M1) to pro-healing (M2A) to pro-remodeling (M2C) phenotypes.

The term "wound macrophage" as used herein refers to a hybrid population of macrophages in a wound including a spectrum of macrophage phenotypes and subtypes that include, but are not limited to, M0, M1, and M2 (including M2A and M2C) macrophages.

The term "M0 macrophage" as used herein refers to a subtype of macrophages that are resting or unactivated (unpolarized).

The term "M1 macrophage" as used herein refers to a subtype of macrophages that are classically activated or exhibit an inflammatory macrophage phenotype. M1 macrophages are activated by LPS and IFN-γ, and secrete high levels of IL-1-beta, TNF-alpha, and IL-12. M1 macrophages also include macrophages that exhibit a hybrid phenotype that is predominantly the M1 phenotype.

The term "M2A macrophage" as used herein refers to a macrophage subtype of pro-healing macrophages. M2A macrophages are involved in immunosuppression and immunoregulation. They are activated by IL-4 and IL-13 and secrete high levels of CCL18 and CCL22. M2A macrophages also include macrophages that exhibit a hybrid phenotype that is predominantly the M2A phenotype.

The term "M2C macrophage" as used herein refers to a macrophage subtype of pro-remodeling macrophages. M2C macrophages are involved in matrix remodeling and tissue repair. They are activated by IL-10 and secrete high levels of MMPs, in particular MMP9. M2C macrophages also include macrophages that exhibit a hybrid phenotype that is predominantly the M2C phenotype.

The term "M2" broadly refers to macrophages that function in constructive processes like wound healing and tissue repair. Major differences between M2A and M2C macrophages exist in wound healing.

"Pharmaceutically acceptable" refers to those properties and/or substances that are acceptable to the patient from a pharmacological/toxicological point of view and to the manufacturing pharmaceutical chemist from a physical/chemical point of view regarding composition, formulation, stability, patient acceptance and bioavailability. "Pharmaceutically acceptable carrier" refers to a medium that does not interfere with the effectiveness of the biological activity of the active ingredient(s) and is not toxic to the host to which it is administered.

As used herein, the term "pharmaceutical composition" or "pharmaceutically acceptable composition" refers to a mixture of at least one compound or molecule useful within the invention with a pharmaceutically acceptable carrier. The pharmaceutical composition facilitates administration of the compound or molecule to a patient. Multiple techniques of administering a compound or molecule exist in the art including, but not limited to, intravenous, oral, aerosol, parenteral, ophthalmic, pulmonary and topical administration.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound or molecule useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound or molecule useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, "sample" or "biological sample" refers to anything, which may contain the cells of interest (e.g., macrophages) for which the screening method or treatment is desired. The sample may be a biological sample, such as a biological fluid or a biological tissue. In one embodiment, a biological sample is a tissue sample including pulmonary arterial endothelial cells. Such a sample may include diverse cells, proteins, and genetic material. Examples of biological tissues also include organs, tumors, lymph nodes, arteries and individual cell(s). Examples of biological fluids include urine, blood, plasma, serum, saliva, semen, stool, sputum, cerebral spinal fluid, tears, mucus, amniotic fluid or the like.

A "sequential controlled release delivery system" refers to a delivery system that may be designed to sequentially release a first agent and a second agent, or more agents. In one embodiment, the delivery system is a biocompatible and biodegradable composition that is capable of releasing one or more agents in a controlled and sequential manner. The delivery system may be injectible and/or implantable into a target site. In another embodiment, the delivery system is programmable to control release of one or more agents in a sequential manner via application of an external stimulus, such as electrical activation, magnetic stimuli, light, ultrasound, heat, pH change, addition of an enzyme, or any other trigger that would activate its release. The concentration released may be controlled through the programming. The controlled release provides both temporally and concentration-dependent release of one or more agents.

A "subject" or "patient," as used therein, may be a human or non-human mammal. Non-human mammals include, for example, livestock and pets, such as ovine, bovine, porcine, canine, feline and murine mammals. Preferably, the subject is human.

As used herein, the terms "treat," treating," "treatment," and the like refer to reducing or improving a disorder and/or symptom associated therewith. It will be appreciated that, although not precluded, treating a disorder or condition does not require that the disorder, condition or symptoms associated therewith be completely ameliorated or eliminated.

As used herein, the term "wound composition" refers to a composition that may be applied to the wound to promote healing or prevent further harm. The wound composition may be a sterile wound cover in direct contact with the wound. The wound composition may include a composition that is administered to a subject in need thereof. The wound composition may be applied to an external or internal wound. The wound composition may be administered to the subject through a delivery system. In some embodiments, the wound composition includes, but is not limited to, a hydrocolloid composition, a hydrogel, a polysaccharide-based composition, a semi-permeable polymeric adhesive film matrix, foam composition, biological composition, and other natural or synthetic polymeric scaffold.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

Delivery Systems

In tissue engineering, a popular strategy for enhancing tissue regeneration is to recapitulate and reinforce the body's natural cellular and molecular mechanisms involved in tissue growth and repair. In various physiological processes, such as angiogenesis and wound healing, a combination of signals is needed at the right dosage and at the right time for the healing process to occur. Therefore, treatment strategies that enable temporally- and spatially-controlled provisions of signals are highly favorable in tissue engineering.

The present invention describes the discovery of methods and composition to induce macrophage conversion to promote wound healing. In one aspect, the invention includes a method of inducing macrophage conversion in a wound comprising inducing conversion of a first population of wound macrophages, including M0 and/or M1 wound macrophages, to M2A macrophages and then converting a second population of wound macrophages, including M2A and/or other wound macrophages, to M2C macrophages, wherein inducing conversion of the macrophages comprises administering at least one agent from a delivery system to the macrophages.

A variety of controlled-release delivery systems have been developed in the past for sequential release of agents such as cytokines, growth factors, or genes. In one embodiment, the agent that induces conversion of macrophage includes, but is not limited to, IL-4, an IL-4 agonist, a molecule that activates an IL-4 signaling pathway, IL-10, an IL-10 agonist, a molecule that activates an IL-10 signaling pathway, dexamethasone, a dexamethasone analog, and combinations thereof.

Polymeric matrices, either natural (such as gelatin, chitosan, hyaluronic acid) or synthetic (PLGA, PLA, etc.) may be used as carriers for delivery of agents. In these approaches, agents are either physically or chemically attached to or encapsulated within the polymeric matrix. By controlling a variety of parameters such as the amount of agent loaded on or into the matrix, properties of the matrix such as its porosity and surface charge, degradation or swelling rate of the matrix, etc., one can control the rate of release of agents from these matrices. In one embodiment, the delivery system is a wound composition, such as a hydrocolloid composition, a hydrogel, a polysaccharide-based composition, a semi-permeable polymeric adhesive film matrix, foam composition, biological composition, and polymeric scaffold. In another embodiment, the delivery system is a wound composition that induces macrophage conversion from M0 and/or M1 wound macrophages to M2A macrophages and then induces macrophage conversion of M2A and/or other wound macrophages to M2C macrophages.

In general, delivery systems may be controlled by diffusion, swelling, erosion, or by an external stimulus. In diffusion-based systems, release is controlled by diffusion down concentration gradient. In swelling-based release, water penetration will cause swelling of the matrix, allowing agent to diffuse out. Erosion-based release, in which release can be achieved through either surface or bulk erosion, is governed by physical or chemical erosion of the matrix. In stimuli-controlled delivery systems, a stimulus is needed to trigger release. This stimulus can be endogenous, for example change of pH in surrounding tissue could trigger release of agent, or it can be exogenous such as light or ultrasound, in which exposure of the carrier to external factors result in agent release.

One of the simplest yet most common strategies to achieve sequential release is incorporation of polymeric vesicles encapsulating one agent inside a secondary carrier loaded with another agent. Because the agent encapsulated inside the vesicles faces two barriers to release (vesicle plus secondary carrier vs. secondary carrier only), the amount of time the agent is present is related to physical properties of each carrier polymer, resulting in a sequential release profile. This approach can be extended for delivery of one or more agents by varying the properties or polymer content of the vesicles, such as crosslinking density to achieve vesicles with varying release rates.

Another strategy is layer-by-layer assembly of polymeric matrices or scaffolds. In this approach, each layer comprises certain agents and release of encapsulated agents is achieved in the order of layers, with the agent encapsulated within the most outer layer being released first. A similar approach can be utilized in delivery of multiple agents from electrospun fibers comprising of multiple layers, each withholding layer comprising a different agent.

Affinity-based delivery systems are another class of controlled release systems that rely on immobilizing and releasing agents based on non-covalent interactions including charge, hydrophobic interactions, hydrogen bonding, or van der Waals forces. One example of an affinity-based delivery system is a heparin-based delivery system for heparin-binding growth factors. In a similar way, the affinity interaction between peptides and various growth factors have been exploited in designing controlled release systems. For instance, in one embodiment a phage display library may be used to identify peptide domains with varying affinities for a cytokine or growth factor. The release of the cytokine or growth factor from the binding peptide matrix allows a comparison of peptide domains with varying affinities. Cyclodextrin (CD) is another molecule with a unique configuration with a relatively hydrophilic exterior and hydrophobic interior. This structure enables CD to complex with small hydrophobic agents and molecules, changing the property of the agent to be more hydrophilic. This non-covalent interaction has been utilized in various delivery systems. In another embodiment, the delivery system is selected from the group consisting of sequential controlled-release delivery system such as an affinity-based delivery system, and layer-by-layer delivery system.

Hydrogel Compositions

The present invention describes the actions of distinct macrophage phenotypes as useful for each phase of the healing process. Dysfunctional macrophage behavior appears to be the underlying basis for chronic wounds. By correcting macrophage behavior and sequentially transitioning macrophages from pro-inflammatory to pro-healing to pro-remodeling phenotypes, normal wound healing can occur. For example, the controlled release of an agent capable of inducing macrophage conversion in a sequential manner would cause downregulation of M0 and/or M1 wound macrophage behavior and sequential upregulation of M2A and M2C macrophage phenotypes, respectively.

A treatment strategy that facilitates the transition of macrophages at appropriate times would restore the natural healing process. The present invention describes methods and compositions for sequentially inducing macrophage conversion by taking advantage of hydrogel microsphere technologies to sequentially present macrophage phenotype-conversion factors to macrophages.

One aspect describes a method of sequentially inducing macrophage conversion in a wound by administering an agent from a delivery system, such as hydrogel microspheres, to the wound. In such an embodiment, the hydrogel microspheres include an inner core of hydrogel polymers bound to IL-10 and an outer shell of hydrogel polymers bound to IL-4; exposing M0 and/or M1 wound macrophages in the wound to IL-4 that is released from the outer shell, where the exposure of the M0 and/or M1 wound macrophages to the released IL-4 induces conversion to M2A macrophages; and exposing the M2A and/or other wound macrophages to IL-10 that is released from the inner core, where exposure of the M2A and/or other wound macrophages to the released IL-10 induces conversion to M2C macrophages. In one embodiment, the step of exposing the M2A and/or other wound macrophages to IL-10 includes exposing other macrophages in the wound to IL-10, such as macrophages that have newly arrived to the wound.

In another embodiment, the delivery system comprises hydrogel microspheres such as those comprising an inner core of hydrogel polymers bound to interleukin-10 (IL-10) and an outer shell of hydrogel polymers bound to interleukin-4 (IL-4). In yet another embodiment, the delivery system comprises IL-4 bound to hydrogel polymers through a binding molecule, such as the IL-4 covalently bound to an affinity molecule that interacts with the binding molecule. In yet another embodiment, the IL-4 is released by dissociating the IL-4 from the binding molecule. In still yet another embodiment, the delivery system comprises IL-10 bound to hydrogel polymers through a binding molecule, such as the IL-10 is bound to an affinity molecule that interacts with the binding molecule, wherein the binding molecule is bound to the hydrogel polymers. In another embodiment, inducing conversion comprises applying the hydrogel microspheres to the wound, inducing conversion of M0 and/or M1 wound macrophages in the wound to M2A macrophages by exposure to IL-4 that is released from the outer shell of the hydrogel microspheres, and inducing conversion of M2A and/or other wound macrophages to M2C macrophages by exposure to IL-10 that is released from the inner core of the hydrogel microspheres.

In another aspect, a method of sequentially inducing macrophage conversion in a wound comprising administering IL-4 from a delivery system to induce conversion of a first population of wound macrophages, including M0 and/or M1 wound macrophages, in the wound to M2A macrophages, and then administering IL-10 from the delivery system to induce conversion of a second population of wound macrophages, including M2A and/or other wound macrophages, to M2C macrophages. In one embodiment, the administering steps comprise applying hydrogel microspheres to the wound, exposing M0 and/or M1 wound macrophages in the wound to IL-4 that is released from the outer shell, wherein the exposure of the M0 and/or M1 wound macrophages to the released IL-4 induces conversion to M2A macrophages, and exposing the M2A and/or other wound macrophages to IL-10 that is released from the inner core, wherein exposure of the M2A and/or other wound macrophages to the released IL-10 induces conversion to M2C macrophages Hydrogels useful as a microsphere can include a natural polymer, synthetic polymer or combinations of natural and synthetic polymers. Natural polymers can include polymers such as anionic polymers (for example, hyaluronic acid, alginic acid, pectin, carrageenan, chondroitin sulfate, dextran sulfate), cationic polymers (for example, chitosan and polylysine), amphipathic polymers (such as collagen, gelatin, carboxymethyl chitin and fibrin) and neutral polymers (for example, dextran, agarose and pullulan), and their derivatives or neutral polymers known in the art. Synthetic polymer hydrogels include, but are not limited to, polymers such as polyesters, poly(ethylene glycol), poly(lactic acid), poly(lactic-co-glycolic acid), polycaprolactone, poly(hydroxyl butyrate); poly(propylene fumerate-co-ethylene glycol)±acrylate end groups, poly(poly(ethylene glycol)/poly (butylene oxide)terephthalate), and any derivatives thereof or known in the art. Synthetic polymer hydrogels may include, for example, other polymers such as: poly(ethylene glycol)-bis-(poly(lactic acid)-acrylate); poly(ethylene glycol)±cyclodextrins; poly(ethylene glycol)-g-poly(acrylamide-co-Vamine); polyacrylamide; poly(N-isopropyl acrylamide-co-acrylic acid); poly(N-isopropyl acrylamide-co-ethyl methacrylate); poly(vinyl acetate)/poly(vinyl alcohol); poly(N-vinyl pyrrolidone); poly(methyl methacrylate-co-hydroxyethyl methacrylate); polyacrylonitrile-co-allyl sulfonate); poly(biscarboxy-phenoxy-phosphazene); poly (glucosylethyl methacrylate-sulfate), and derivatives thereof or synthetic polymers known in the art. Combinations of natural and synthetic polymers may include polymers such as poly(polyethylene glycol-co-peptides), alginate g-(polyethylene oxide-polypropylene oxide-polyethylene oxide), poly(polylactic-co-glycolic acid-co-serine), collagen-acrylate, alginate-acrylate, poly(hydroxyethly methacyrlate-g-peptide), poly(hydroxyethyl methacyrlate/collagen), hyraluronic acid-g-N-isopropyl acrylamide), or any combination of natural and synthetic polymers described here or known in the art.

In one embodiment, IL-4 is bound to the hydrogel polymers through a binding molecule. The binding molecules can include, but are not limited to, avidin, avidin-like polymers such as NEUTRAVIDIN®, CAPTAVIDIN® and streptavidin, tamavidins, and other biotin-binding proteins. In another embodiment, antigen from an antibody/antigen pair, heparin, ligand, and other molecules from an affinity-based system can be used in a similar manner to link IL-4 to the hydrogel polymer. In yet another embodiment, the binding molecule is avidin. In a particular embodiment, the IL-4 is covalently bound to an affinity molecule that interacts with the binding molecule.

Affinity molecules useful with the hydrogel microspheres described herein can include biotin, 4'-hydroxyazobenzene-2-carboxylic acid (HABA), other avidin binding molecules, an antibody from an antibody/antigen pair, a heparin-binding protein, a receptor, ligand binding domain from a receptor, and other affinity molecule from an affinity-based system. Other ligands with varying affinity for avidin that may be useful herein are described in Kuhn and Kollman, *J Med Chem*, 43: 3786-3791 (2000). It is also possible to custom-design peptides with customized affinity for avidin and avidin analogs (such as neutravidin and streptavidin), as in Kay et al., *Gene*, 128: 59-65 (1993), and Meyer et al., *Chemical Biology and Drug Design*, 68: 3-10 2006. In another particular embodiment, the IL-4 is released by dissociating the IL-4 from the binding molecule.

In another embodiment, IL-10 is bound to the hydrogel polymers through a binding molecule. In a particular embodiment, the IL-10 is bound to an affinity molecule that interacts with the binding molecule, wherein the binding molecule is bound to the hydrogel polymers. Examples of affinity molecules that interact with binding molecules include, but are not limited to, biotin, 4'-hydroxyazobenzene-2-carboxylic acid (HABA), and other avidin or avidin-like binding molecules.

In yet another embodiment, IL-10 is released by enzymatic cleavage of the bound IL-10 by an enzyme that is present in the wound. The enzyme may be secreted by any cells in a wound including but not limited to any subtype or phenotype of macrophage described herein such as M0 and M2C macrophages. In another embodiment, the secretion is inhibited in the presence of M2A macrophages. Enzymes that are secreted from macrophage include, but are not limited to, hydrolases like elastase and lysosomal hydrolases and proteases like collagenases, gelatinases, matrix metalloproteases (for example any of MMP1, MMP2, MMP3, MMP4, MMPS, MMP6, MMP7, MMP8, MMP9, MMP10, MMP11, MMP12, and MMP13). In one particular embodiment, the secreting enzyme comprises matrix metalloproteases (MMP) that cleave the bound IL-10 from the inner core. Examples of MMPs can include MMP1 through MMP13, which also include collagenases, gelatinases and elastases.

Also described herein are methods of preparing a hydrogel microsphere for wound healing. In one aspect, the method includes binding IL-10 to the hydrogel microsphere, exposing the hydrogel microsphere with bound IL-10 to IL-4, and displacing the bound IL-10 on an outer thickness of the hydrogel microsphere with IL-4, wherein the IL-4 binds to the hydrogel microsphere. In another aspect, IL-10 could be loaded within a hydrogel microsphere, and then the entire microsphere could be further encapsulated with an outer layer containing IL-4.

In one embodiment, agent capable of inducing macrophage conversion, such as IL-4, an IL-4 agonist, a molecule that activates an IL-4 signaling pathway, IL-10, an IL-10 agonist, a molecule that activates an IL-10 signaling pathway, dexamethasone, a dexamethasone analog, and combinations thereof, is bound to a polymer, such as a hydrogel microsphere, either covalently or non-covalently. In another embodiment, the agent, such as IL-4 or IL-10, is bound to a binding molecule bound to the polymer. In one embodiment, the agent, such as IL-4 or IL-10, is bound to an affinity molecule that interacts with the binding molecule that is bound to the polymer. In another embodiment, the IL-10 is bound to the polymer through a matrix metalloprotease (MMP) sensitive peptide. In yet another embodiment, the agent, such as IL-4 or IL-10, is bound through a matrix metalloprotease (MMP) sensitive peptide to an affinity molecule that interacts with avidin, where avidin is bound to the polymer. In yet another embodiment, the agent, such as IL-4 or IL-10, is covalently bound to the polymer. In a particular embodiment, the polymer is exposed to IL-4 covalently bound to a higher affinity molecule, where the higher affinity molecule interacts with avidin and has a higher association constant and/or lower dissociation constant than the affinity molecule bound to IL-10. This would result in the displacement of the affinity molecule bound to IL-10 with the higher affinity molecule bound to IL-4.

The invention further provides, in one aspect, hydrogel microspheres. The hydrogel microsphere includes an inner core of hydrogel polymers bound to IL-10 through an inner core binding molecule, wherein the IL-10 is bound to a small molecule that interacts with the inner core binding molecule, and an outer shell of hydrogel polymers bound to an outer shell binding molecule comprising IL-4 bound to a small molecule with a higher affinity to interact with the outer shell binding molecule than the IL-10 bound small molecules.

In one embodiment, the agent, such as IL-4 or IL-10, is covalently bound to the first molecule through a peptide linker. The linker can include a peptide sequence. The peptide sequence can include an enzyme cleavage site, such as a MMP cleavage recognition site, VPLSxLYSG, where x denotes the cleavage site, or any other peptide, including those described in Patterson and Hubbell, *Biomaterials*, 31: 7836-7845 (2010). The linker can include another recognition site for a macrophage-secreted enzyme, such as a hydrolase. In a particular embodiment, the peptide linker includes a matrix metalloproteinase cleavage sequence. In another particular embodiment, the inner core binding molecule and outer shell binding molecule are avidin. In still another particular embodiment, the first molecule bound to IL-10 is 4'-hydroxyazobenzene-2-carboxylic acid (HABA). In still another particular embodiment, the higher affinity second molecule bound to IL-4 is biotin. In another embodiment, the IL-4 is covalently bound to the higher affinity second molecule.

Pharmaceutical Compositions

The present invention also includes methods for treating a chronic wound. In one aspect, the method includes administering to the wound at least one agent from a delivery system wherein the agent induces sequential conversion of a first population of wound macrophages, including M0 and M1 wound macrophages, in the wound to M2A macrophages and a second population of wound macrophages, including M2A and newly arrived wound macrophages, to M2C macrophages, wherein the sequential conversion of the wound macrophages promotes tissue remodeling.

In another aspect, the invention includes a method of treating a chronic wound comprising exposing the wound to hydrogel microspheres, wherein the hydrogel microspheres comprise an inner core of hydrogel polymers bound to interleukin-10 (IL-10) and an outer shell of hydrogel polymers bound to interleukin-4 (IL-4). In one embodiment, the method further comprising sequentially converting a first population of wound macrophages, including M0 and M1 wound macrophages, in the wound to M2A macrophages by exposing the first population of wound macrophages to IL-4 and converting a second population of wound macrophages, including M2A and newly arrived wound macrophage, to M2C macrophages by exposing the second population of wound macrophages to IL-10. Therefore, by sequentially converting wound macrophages in the wound to M2A macrophages by exposing the wound macrophages to IL-4 and converting the wound macrophages to M2C macrophages by exposing the second population of wound macrophages to IL-10, the natural healing process is restored in the wound.

The invention also encompasses the use of a pharmaceutical composition of the invention to practice the methods of the invention. Such a pharmaceutical composition may be provided in a form suitable for administration to a subject, and may be comprise one or more pharmaceutically acceptable carriers, one or more additional ingredients, or some combination of these. The at least one composition of the invention may comprise a physiologically acceptable salt, such as a compound contemplated within the invention in combination with a physiologically acceptable cation or anion, as is well known in the art.

Pharmaceutical compositions that are useful in the methods of the invention may be suitably developed for parenteral, topical, or another route of administration. The route(s) of administration will be readily apparent to the skilled artisan and will depend upon any number of factors including the type and severity of the wound being treated, the type and age of the veterinary or human patient being treated, and the like.

Pharmaceutical formulations of the hydrogel microspheres described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

In one embodiment, the hydrogel microspheres of the invention are formulated using one or more pharmaceutically acceptable excipients or carriers. In one embodiment, the pharmaceutical compositions of the invention comprise a therapeutically effective amount of at least one agent that induces sequential conversion of macrophages and a pharmaceutically acceptable carrier. Pharmaceutically acceptable carriers, which are useful, include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", fourth edition (Sambrook, 2012); "Oligonucleotide Synthesis" (Gait, 1984); "Culture of Animal Cells" (Freshney, 2010); "Methods in Enzymology" "Handbook of Experimental Immunology" (Weir, 1997); "Gene Transfer Vectors for Mammalian Cells" (Miller and Calos, 1987); "Short Protocols in Molecular Biology" (Ausubel, 2002); "Polymerase Chain Reaction: Principles, Applications and Troubleshooting", (Babar, 2011); "Current Protocols in Immunology" (Coligan, 2002). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the compositions and methods of the invention, and are not intended to limit the scope of what the inventors regard as their invention.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out embodiments of the present invention, and are not to be construed as limiting in any way.

The Results of Example 1 disclosed herein are now described.

Example 1

Hydrogel Microspheres Capable of Inducing Macrophage Conversion

Figure 1:
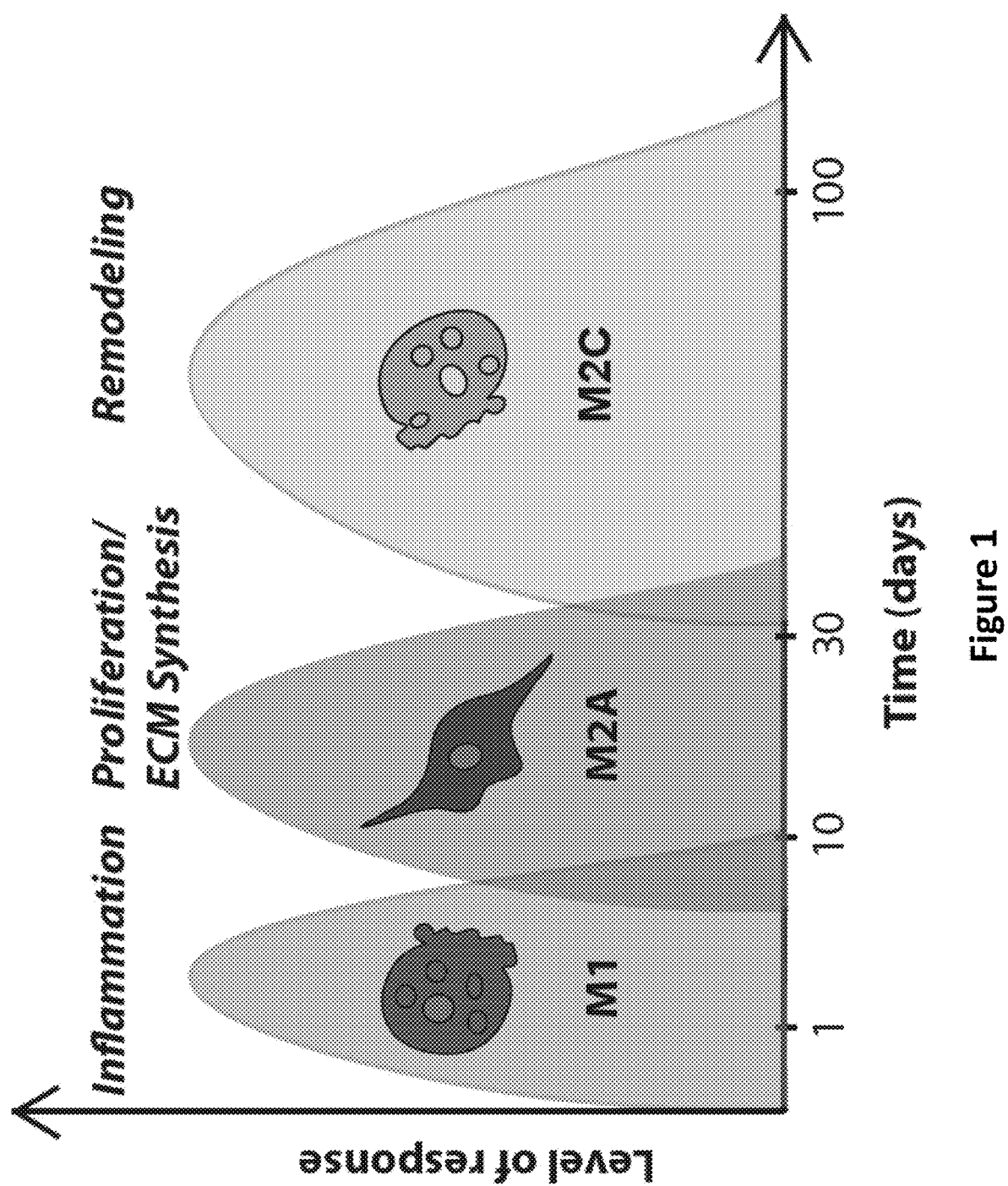
FIG. 1 is a schematic showing the stages of wound healing are controlled by different macrophage phenotypes. M1 macrophages dominate the initial stage, which is characterized by inflammation; M2A macrophages dominate the next stage, characterized by cell proliferation and deposition of extracellular matrix (ECM) components/tissue; and M2C macrophages dominate the final phase of wound healing, characterized by tissue remodeling.

The hydrogel microsphere technology described herein converts inflammatory macrophages, also known as M1, to M2A macrophages that inhibit inflammation and promote cell proliferation and deposition of extracellular matrix components (the second phase of normal healing). The inner core of the hydrogel microspheres provide a second phase that promotes polarization to the M2C phenotype, which causes remodeling of the fibrous tissue to healthy tissue. FIG. 1 shows the stages of wound healing controlled by different macrophage phenotypes. M1 macrophages dominate the initial stage, which is characterized by inflammation; M2a macrophages dominate the next stage, characterized by cell proliferation and deposition of extracellular matrix (ECM) components/tissue; and M2c macrophages dominate the final phase of wound healing, characterized by tissue remodeling.

By linking the release of IL-10 to the departure of the M2A macrophage population, the hydrogel microspheres ensure the completion of M2A macrophage behavior before the actions of the M2C macrophages. Moreover, the hydrogel microspheres allow for the delayed release of IL-10 for periods of days to weeks to months to years, because the hydrogel microspheres depend on the actions of a continually replenishing supply of macrophages in the wound environment. Such delayed release is difficult, if not impossible, to achieve with conventional methods of controlled release factors from hydrogels.

FIG. 2A is a schematic illustrating the control over macrophage behavior in a chronic wound, with resulting effects on the wound healing process. M1 macrophages are present in high numbers in chronic wounds. FIG. 2B is a schematic illustrating the flowable slurry of hydrogel microspheres is used to fill the wound. FIG. 2C is a schematic illustrating that the microspheres first release M2A-promoting cytokines such as IL-4, which converts any macrophages in the vicinity into M2A macrophages that in turn promote synthesis of extracellular matrix (ECM) and tissue repair. FIG. 2D is a schematic illustrating M2C-promoting cytokine is released after M2A-promoting cytokine, which causes the conversion of any macrophages in the vicinity to convert to an M2C phenotype after a period of time that M2A macrophages dominate. The M2C macrophages promote remodeling of the tissue and finish the wound healing process. Note that this process would work for any molecule besides IL-4 that promotes the M2A phenotype and any molecule besides IL-10 that promotes the M2C phenotype.

Figure 3:
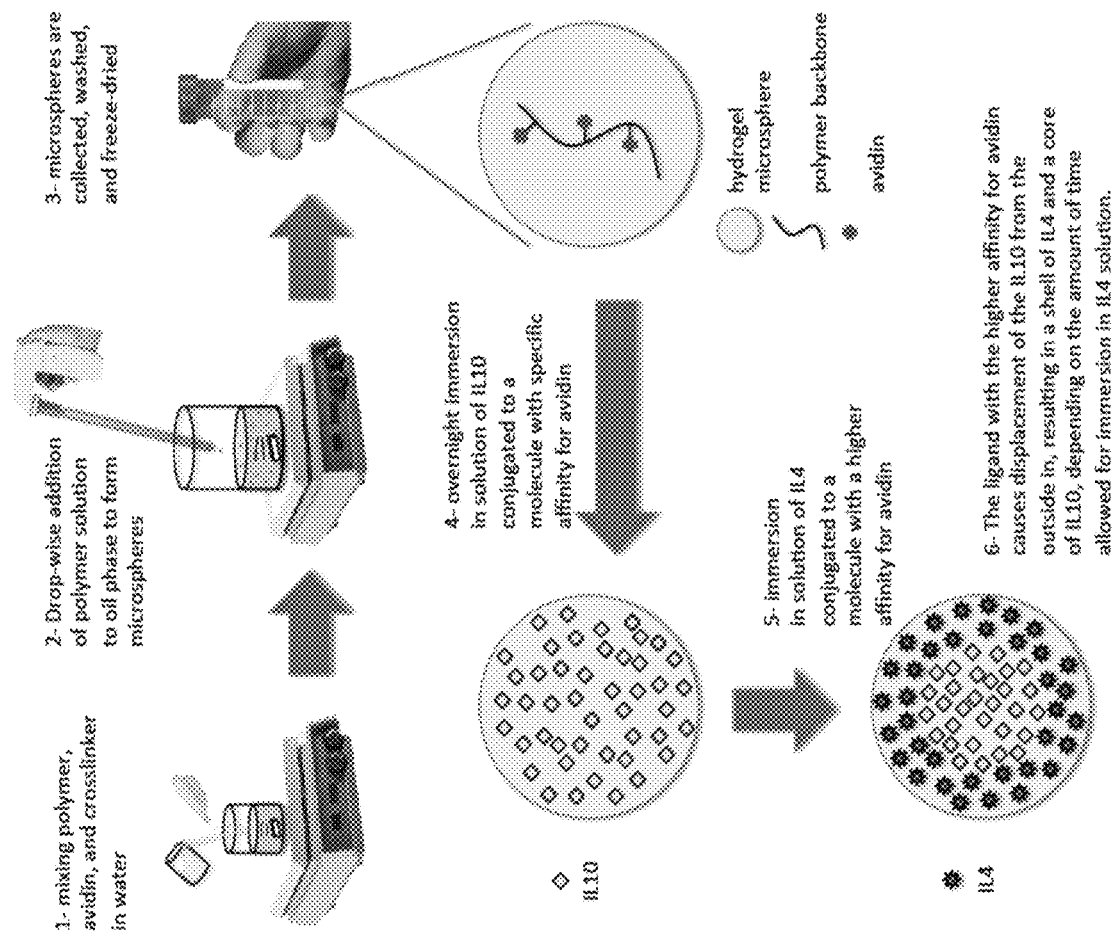
FIG. 3 shows how the hydrogel microspheres were prepared using molecules with different affinities for the protein avidin. Avidin was crosslinked to the polymer using covalent or transient conjugation in an aqueous preparation (1), which was then added dropwise to an oil phase (2), forming an emulsion. The size of the microspheres was dependent on the speed of stirring or homogenization. The hydrogel microspheres, which now contained avidin directly conjugated to the polymer, were collected by filtration or centrifugation, washed, and freeze-dried (3). The microspheres were immersed in a solution of IL-10 that was conjugated to a molecule, such as a ligand or peptide, with specific and high affinity for avidin. After a sufficiently long period of time (such as overnight), the IL-10 was distributed throughout the hydrogel microspheres and bound to the avidin on the polymer via ligand-avidin interactions (4). Then, the microspheres were immersed in a solution of IL-4 conjugated to a molecule with a higher affinity for avidin than the one conjugated to IL-10 (5), so that the IL-10 was displaced from the avidin when the IL-4 was present. This occurred from the outside in because of simple diffusion, creating a shell of IL-4 and a core of IL-10 (6). The thickness of the shell depended on the amount of time allowed for diffusion of the IL-4 into the hydrogel spheres. IL-10 molecules in the core of the microspheres were trapped inside the inner core due to the high concentration of available binding sites provided by avidin and high affinity between the ligand and avidin molecules. However, when IL-10 was conjugated to a ligand with affinity for avidin via a matrix metalloprotease (MMP)-sensitive peptide, IL-10 molecules were released by the action of MMPs that diffused into hydrogels (see FIGS. 2A-2D). Note that this process would work for any ligand-protein interaction, provided that the affinity of the ligand attached to IL-4 for the polymer is higher than the one attached to IL-10, so that the IL-4 is loaded in the outer shell and IL-10 is in the core. This process would also work if IL-10 were directly conjugated to the hydrogel polymer, so that degradation of the hydrogel polymer itself causes release of IL-10. This process would also work if the linkage between IL-10 and the binding molecule is selectively degraded by enzymes released by M0 (resting/unactivated) or M2C macrophages, but not M2A macrophages.

FIG. 3 shows how the hydrogel microspheres are prepared using molecules with different affinities for the protein avidin. The thickness of the shell depends on the amount of time allowed for diffusion of the IL-4 into the hydrogel spheres. IL-10 molecules in the core of the microspheres are trapped inside the inner core due to the high concentration of available binding sites provided by avidin and high affinity between the ligand and avidin molecules. However, when IL-10 is conjugated to a ligand with affinity for avidin via a matrix metalloprotease (MMP)-sensitive peptide, IL-10 molecules are released by the action of MMPs that diffuse into hydrogels (see FIGS. 2A-2D). Note that this process would work for any ligand-polymer interaction, provided that the affinity of the ligand attached to IL-4 for the polymer is higher than the one attached to IL-10, so that the IL-4 is loaded in the outer shell and IL-10 is in the core. This process would also work if IL-10 were directly conjugated to the hydrogel polymer, so that degradation of the hydrogel polymer itself causes release of IL-10.

Figure 4:
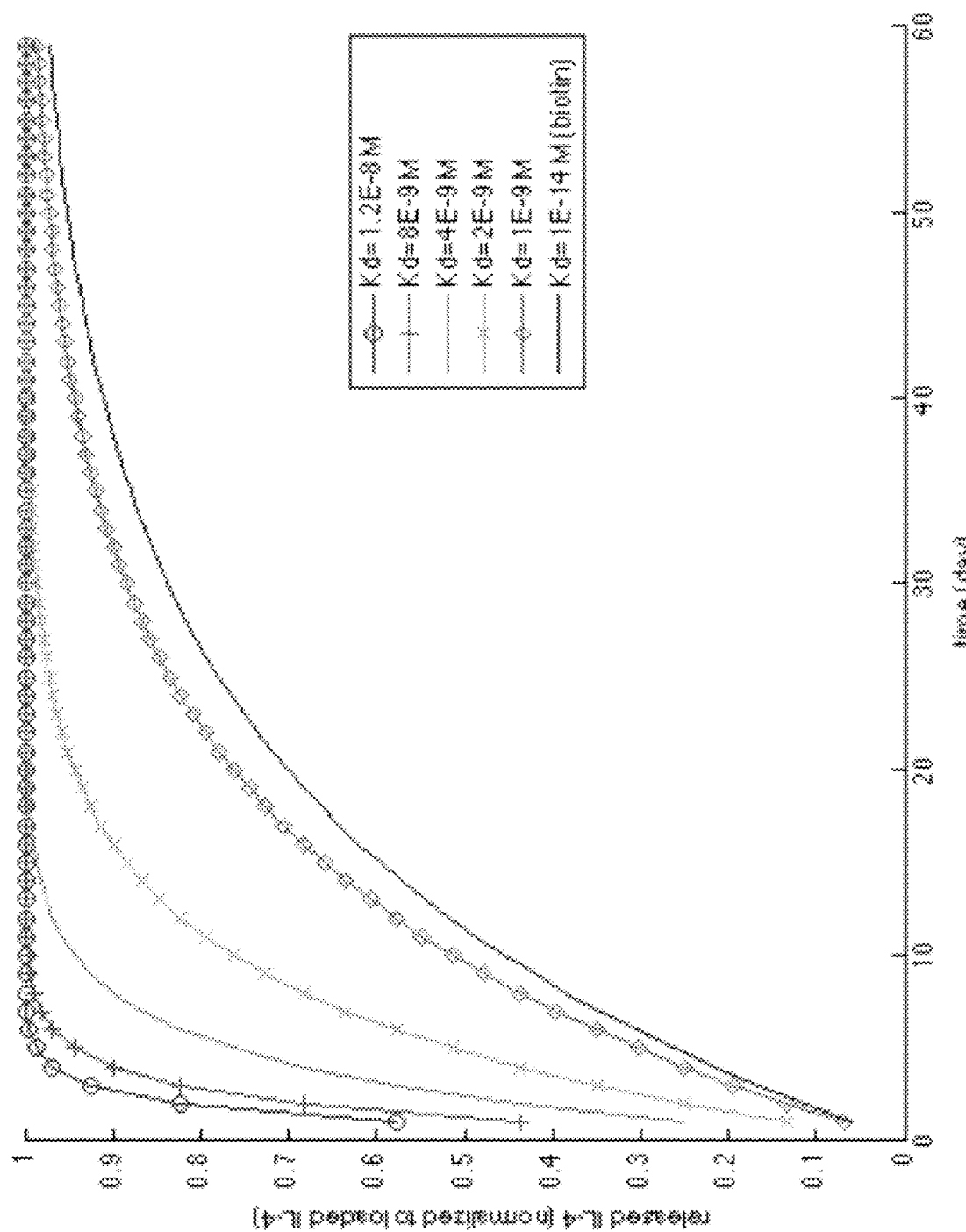
FIG. 4 demonstrates the level of control over release of IL-4 that can be achieved by varying the affinity for the ligand bound to IL-4 and avidin, which is bound covalently or transiently to the hydrogel polymer. When IL-4 is conjugated to small molecules with varying affinity for avidin, the following equation describes the interactions between IL-4 and avidin.

FIG. 4 demonstrates the level of control over release of IL-4 that can be achieved by varying hydrogel properties. FIG. 5 demonstrates how delayed release of IL-10 is achieved via control over macrophage phenotype. FIG. 6 demonstrates that the rate of IL-10 release can be controlled by varying the sequence of the MMP-sensitive peptide linkage to change the ability of MMPs to degrade it (Kcat). FIG. 7 shows that sequential release of IL-4 and IL-10 can be achieved using this technology, thus causing sequential activation of M2A and M2C phenotypes, and sequential phases of proliferation and remodeling.

FIG. 8 is a panel of images showing the conversion of macrophage markers into a single combinatorial score that describes the expression profile of macrophage markers in human healing and nonhealing diabetic ulcers. (a) Sequential M1-to-M2 activation profile in normal wound healing. (b) Schematic of in vitro experiments and clinical study design. (c) Transcriptional profiling of macrophages polarized in vitro to the M1 or M2 phenotypes using known markers as described in (Spiller et al., 2014) (mean +/− SEM, n=5). (d) Principal component analysis of the gene expression data of in vitro polarized macrophages. (e) M1/M2 score applied to in vitro polarized macrophages (mean +/− SEM, n=5). (f) Change in M1/M2 score (relative to normal skin) over time in healing acute wounds (mean +/− SEM, n=3 pooled data from 15 samples), using data obtained from (Greco et al., 2010). (g) Change in M1/M2 score (relative to the first time point) over time in healing vs. nonhealing diabetic wounds over 4 weeks from the initial visit (mean +/− SEM, n=3 healing and n=4 nonhealing). (h) Comparison of mean fold change of M1/M2 score (relative to first time point) between healing and nonhealing diabetic ulcers at 4 weeks (mean +/− SEM, n=3 healing and n=4 nonhealing). Statistical significance was analyzed using unpaired two-sided Student's t test. *$P<0.05$ and **$P<0.01$.

FIGS. 9, 10, and 11 show the higher expression of matrix metalloprotease-9 (MMP9), MMP8, and MMP7 in M2C macrophages identified by RNAseq, suggesting a role in the remodeling stage of the wound healing process. MMP9 expression is inhibited in M2a macrophages. M0 (resting) macrophages also express and secrete high levels of MMP9, indicating that this behavior can be used to cause release of proteins bound to polymers via MMP-sensitive peptide linkages.

FIG. 12 shows higher expression of the MMP inhibitor TIMP3 (tissue inhibitor of metalloprotease 3) in M2A macrophages, further highlighting their inhibited ability to cleave certain MMP-sensitive sequences, and further suggesting a role in the tissue deposition phase of wound healing.

FIG. 13 is a panel of images showing that selective binding of streptavidin Dylight 594 to biotinlyated collagen scaffolds was observed, but not to nonbiotinylated scaffolds.

FIG. 14 is a graph showing release of streptavidin Dylight 594 from biotinylated vs nonbiotinylated gelatin disks (10% wt). Biotinylation cause delayed release of streptavidin from gelatin disks. FIG. 15 is a graph showing release of streptavidin Dylight 594 from biotinylated collagen scaffolds, and from biotinylated scaffolds that have been coated with 10 or 20 wt % gelatin. These results demonstrate that the release of protein is a function of both affinity interactions between biotin and avidin and diffusion (because release was delayed in coated scaffolds).

Example 2

Dexamethasone-Induced Macrophage Conversion

Nanodiamond (ND) produced by detonation synthesis commercially is a novel carbon nanomaterial which delivers many properties of diamond at a nanoscale, such as Superior mechanical and thermal properties, chemical resistance, small and uniform particle diameter of ~5 nm, large, accessible and tunable surface covered with a large number of various functional groups, no cytotoxicity and good biocompatibility.

Dexamethasone is a glucocorticoid that is used as a broad spectrum anti-inflammatory drug. FIG. 16 is a panel of images that show that diffusion into hydrogels can be used to control the thickness of the shell/core.

Before attaching this drug to nanodiamond particles for drug delivery, reverse transcription polymerase chain reaction (RT-PCR) was used to clarify the effect dexamethasone had on macrophage conversion and phenotype (FIG. 17). Because of its surface tunability and small size, ND had already proven itself to be an excellent platform for drug adsorption.

A panel of markers analyzed by RT-PCR showed that TNF-alpha, CCR7 and IL-1beta associated with M1 macrophage (FIG. 18), while CD206, MDC and TIMP-3 associated with M2A macrophage (FIG. 19) and CD163 with M2C macrophage (FIG. 20). FIG. 20 is a graph showing RT-PCR analysis of CD163 (an M2c marker). The results showed that the addition of dexamethasone (DEX) to macrophages of any phenotype caused their conversion to the M2c phenotype.

FIG. 21 is a panel of graphs showing a correlation analysis of relationships between macrophage phenotype and the fibrous capsule formation, a model of fibrosis, surrounding model biomaterials implanted subcutaneously in mice for 3 days to 3 weeks. Results showed that M1 macrophages (as indicated by iNOS expression) were not correlated with fibrosis, while M2 macrophages (as indicated by Arg1 expression) were highly correlated with fibrosis (Pearson's correlation coefficient of 0.948).

The Materials and Methods used in the performance of Example 1 disclosed herein are now described Conjugation of Ligands/Peptides to Proteins Small molecules or peptides with affinity for avidin and avidin-based polymers were conjugated to the proteins IL-4 and IL-10 using bioconjugation techniques, such as EDC/NHS chemistry. Example small molecules include biotin, 4'-hydroxyazobenzene-2-carboxylic acid (HABA), and ligands and peptides described in Kuhn and Kollman, *J Med Chem*, 43: 3786-3791 (2000), Kay et al., *Gene* 128: 59-65 (1993), and Meyer et al., *Chemical Biology and Drug Design*, 68: 3-10 (2006).

IL-10 was conjugated to the ligand via an enzymatically degradable linkage using sequential bioconjugation techniques. For example, HABA was incubated in EDC to convert the carboxylic acid groups to amine-reactive groups, which then reacted with the N-terminus of the enzymatically degradable peptide. After purification (separation chromatography), the HABA-linked peptide was incubated again in EDC, converting the C-terminus of the peptide to an amine-reactive group, which covalently bound to the N-terminus of IL-10 upon addition of that protein.

Avidin Conjugation to the Hydrogel Polymer

A solution of avidin in PBS (approximately 10-100 mM) was added to a solution of gelatin in PBS (about 1-10 wt %) while stirring. EDC and NHS were used to covalently link the two proteins. The mixture was immediately used for hydrogel microsphere preparation. Alternatively, avidin can be conjugated non-covalently to the hydrogel polymer by first conjugating biotin or other avidin-binding ligands to the hydrogel polymer, and subsequently incubating with avidin, either before of after hydrogel microsphere preparation.

Hydrogel Microsphere Preparation

In the preparation, 25 mL of avidin-conjugated gelatin was dispersed in 125 mL of olive oil to form a water-in-oil emulsion. After 45 min of stirring at 60 rpm, the temperature was dropped to approximately 4° C. to facilitate physical crosslinking of microspheres. After 15 min, 50 ml of chilled acetone was added, followed by another 1 hr of continuous stirring. The microspheres were collected by centrifugation at 1000 rpm for 5 min, and washed several times with acetone and isopropyl alcohol to remove residual oil. Collected microspheres were sieved to a desired size and freeze-dried for future use.

Gelatin microspheres (10% wt) were also prepared by a water-in-oil emulsion gelation technique. Dry microspheres were mixed with saline. The microspheres hydrated to form a viscous slurry. The hydrated microspheres formed a syringe flowable and space filling regenerative matrix.

Affinity-Based Drug Loading

In the experiment, 500 mg of dried hydrogel microspheres were immersed for a sufficient period of time (such as overnight) in a solution of IL-10 (about 100-1000 ng/ml) that was conjugated to the avidin-binding molecule to form microspheres uniformly loaded with IL-10 bound to avidin, which was itself bound to the hydrogel polymer (in this case, gelatin). Then, in order to form a shell of IL-4, the microspheres were transferred to a solution of IL-4 (about 100-1000 ng/ml) that was conjugated to a molecule with higher affinity for avidin, such as biotin. This caused the IL-4 to displace the IL-10 from the avidin. The process occurred by diffusion, which occurs from the outside in. Thus, the thickness of the IL-4-loaded shell was controlled by the amount of time allowed for diffusion. The microspheres were then washed with PBS to remove unbound proteins.

Mixing of Dry Microspheres with Saline to Make the Final Preparation

Dried hydrogel microspheres impregnated with IL-10 in the core and IL-4 in the shell can be mixed with sterile saline solution to form a viscous slurry. The mixture can be used to fill wounds and provide a regenerative scaffold to support the growth of new tissue.

The Materials and Methods used in the performance of Example 2 disclosed herein are now described.

RT-PCR

Leukocytic monocytes (THP-1s) were seeded in a 24 well plate at a density of $10^6$ cells/mL, then differentiated with 100 ng/ml phorbol 12-myristate 13-acetate (PMA) for 18 hrs followed by 48 hrs of polarization with 100 ng/ml IFNg+100 ng/ml LPS (M1), 40 ng/ml IL4+20 ng/ml IL13 (M2a), or 40 ng/ml IL10 (M2C). Both low doses ($10^{-8}$ M) and high doses ($10^{-6}$ M) of dexamethasone were added during polarization to each of the four macrophage phenotypes. Then, cells were scraped and collected for RT-PCR analysis.

RNA was isolated, quantified, then purified according to our previously described methods (Spiller, et al. Biomaterials, 35:4477-4488, 2014). cDNA was synthesized and amplified using SYBR green using primers specifically designed for macrophage phenotype markers, including TNFα, CCR7, IL1b, CD206/MRC1, MDC/CCL22, TIMP3, and CD163.

A two-way ANOVA was used to determine significance (p<0.05). The experiments were performed with n=3. Additionally, RT-PCR was run in duplicates.

Other Embodiments

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A method of sequentially inducing macrophage conversion in a wound, the method comprising:
   (a) sequentially administering IL-4 to induce conversion of a first population of wound macrophages in the wound to M2A macrophages; and then
   (b) sequentially administering IL-10, dexamethasone, or a dexamethasone analog to induce conversion of a second population of wound macrophages in the wound to M2C macrophages;

wherein steps (a) and (b) are sequentially performed by a delivery system; and wherein the delivery system is a sequential controlled-release delivery system.

2. The method of claim 1, wherein the sequential controlled-release delivery system comprises IL-4 bound to the delivery system through a binding molecule.

3. The method of claim 2, wherein the binding molecule is non-covalently bound to the delivery system.

4. The method of claim 2, wherein the IL-4 is covalently bound to an affinity molecule that interacts with the binding molecule.

5. The method of claim 2, wherein the IL-4 is released by dissociating the IL-4 from the binding molecule.

6. The method of claim 1, wherein the sequential controlled-release delivery system comprises IL-10 bound to the delivery system through a binding molecule.

7. The method of claim 6, wherein the IL-10 is bound to an affinity molecule that interacts with the binding molecule, wherein the binding molecule is bound to the delivery system.

8. The method of claim 6, wherein the affinity molecule is non-covalently bound to the delivery system.

9. The method of claim 6, wherein the bound IL-10 is released by enzymatic cleavage by an enzyme that is present in the wound.

10. The method of claim 9, wherein the enzyme comprises a matrix metalloprotease that cleaves the bound IL-10 from the delivery system.

11. The method of claim 1, wherein the sequential controlled-release drug delivery system is an affinity-based delivery system.

12. The method of claim 1, wherein sequentially inducing macrophage conversion in the wound promotes tissue remodeling.

13. The method of claim 1, wherein when the macrophage conversion in the wound occurs, the wound is treated.

14. The method of claim 1, wherein the wound is a chronic wound.

* * * * *